United States Patent [19]
Nakamura et al.

(10) Patent No.: US 7,867,175 B2
(45) Date of Patent: Jan. 11, 2011

(54) BODY FLUID SAMPLING UNIT

(75) Inventors: Toshihisa Nakamura, Ashigarakami-gun (JP); Daisuke Nishiuchi, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 267 days.

(21) Appl. No.: 11/905,053

(22) Filed: Sep. 27, 2007

(65) Prior Publication Data

US 2008/0077096 A1 Mar. 27, 2008

(30) Foreign Application Priority Data

Sep. 27, 2006 (JP) ............... 2006-263547

(51) Int. Cl.
*A61B 5/00* (2006.01)
*A61F 2/02* (2006.01)
*B65D 81/00* (2006.01)

(52) U.S. Cl. ............ 600/584; 600/583; 606/181; 606/182

(58) Field of Classification Search ......... 600/583, 600/584; 606/181, 182
See application file for complete search history.

(56) References Cited

U.S. PATENT DOCUMENTS

| 4,627,445 | A | * | 12/1986 | Garcia et al. | 600/583 |
| 4,637,403 | A | * | 1/1987 | Garcia et al. | 600/583 |
| 6,338,720 | B1 | * | 1/2002 | Morikawa et al. | 600/584 |
| 7,264,627 | B2 | * | 9/2007 | Perez | 606/181 |
| 7,378,007 | B2 | * | 5/2008 | Moerman et al. | 204/403.03 |
| 2002/0188223 | A1 | * | 12/2002 | Perez et al. | 600/573 |
| 2005/0277849 | A1 | * | 12/2005 | Wong et al. | 600/583 |
| 2006/0047220 | A1 | * | 3/2006 | Sakata et al. | 600/583 |
| 2009/0036915 | A1 | * | 2/2009 | Karbowniczek et al. | 606/182 |
| 2009/0118752 | A1 | * | 5/2009 | Perez et al. | 606/181 |
| 2009/0124931 | A1 | * | 5/2009 | Sakata et al. | 600/583 |

FOREIGN PATENT DOCUMENTS

| JP | WO 00/78203 A2 | 12/2000 |
| JP | 2003-502088 A | 1/2003 |

* cited by examiner

*Primary Examiner*—Max Hindenburg
*Assistant Examiner*—Sean P Dougherty
(74) *Attorney, Agent, or Firm*—Buchanan Ingersoll & Rooney PC

(57) ABSTRACT

A body fluid sampling unit includes a puncture device including a needle having a sharp needle point and a drive mechanism for operating the needle to puncture a living body surface with the needle point, a tip including an introducing section for introducing a body fluid flowing out from a puncture portion of the living body surface punctured with the needle point, a test paper for detecting a predetermined component in the body fluid, and a tip body mounted to a component measuring device for measuring the quantity and/or property of the predetermined component detected by the test paper; and a case including a mechanism containing section for containing the puncture mechanism so that the needle point of the puncture mechanism can be moved by the drive means, and a sampling implement containing section for containing the body fluid sampling implement so that the tip can be taken out.

25 Claims, 22 Drawing Sheets

BODY FLUID SAMPLING UNIT

TECHNOLOGICAL FIELD

The subject matter disclosed herein generally relates to a body fluid sampling unit, and more specifically pertains to a device for obtaining a sample of body fluid such as blood for purposes of detecting a component in the sample.

BACKGROUND DISCUSSION

As the population of diabetics has increased, recent recommendations have called for self-monitoring of blood glucose in which daily variations in the blood glucose level of the patient is monitored by the patient himself/herself. Generally speaking, performing blood glucose measurement involves a puncture implement for puncturing skin and a measuring device for sampling the blood flowing out from the skin punctured by the puncture implement and measuring the blood glucose level in the blood.

An example of the puncture implement is disclosed in Japanese Laid-Open Patent Publication No. 2003-502088 and includes a needle, a case in which to movably contain the needle, and a drive mechanism contained in the case together with the needle and operative to move the needle. The puncture implement of this type is discarded after used once.

In addition, the measuring device is ordinarily used in the condition where a sampling implement which has a reagent capable of reaction with glucose and which functions to receive the spot-like deposition of blood (to sample the blood) is mounted thereto. The sampling implement is detachably mounted to the measuring device, and is discarded after one use, like the puncture implement.

In the past, in performing blood glucose measurement (in sampling blood), the puncture implement and the sampling implement have been prepared individually (separately from each other). Therefore, the preparation for blood glucose measurement is troublesome, and it has been difficult to achieve speedy measurement. In short, the operational aspects associated with performing blood glucose measurement have been poor.

SUMMARY

According to one aspect, a body fluid sampling unit comprises a container having an interior, a needle positioned in the interior of the container and possessing a sharp needle point at a distal end of the needle, at least one spring positioned in the interior of the container, and a body fluid sampling implement removably positioned in the interior of the container. The at least one spring is operatively engageable with the needle and is configured to accumulate a spring bias to be applied to the needle to move the needle in a puncturing direction to puncture a living body surface with the needle point. The body fluid sampling implement comprises an introducing section for conveying body fluid flowing out from a puncture portion of the living body surface punctured with the needle point, a reagent containing part positioned adjacent the introducing section to receive the body fluid conveyed by the introducing section, with the reagent containing part comprising a reagent adapted to interact with a predetermined component in the body fluid, and a mounted section configured to be mounted to a component measuring device for measuring the quantity and/or property of the predetermined component.

According to another aspect, a body fluid sampling unit comprises a puncture mechanism including a needle having a sharp needle point at a distal end thereof and a drive means for operating the needle so as to puncture a living body surface with the needle point, a body fluid sampling implement including an introducing section for introducing a body fluid flowing out from a puncture portion of the living body surface punctured with the needle point, a detecting section for detecting a predetermined component in the body fluid introduced through the introducing section, and a mounted section mounted to a component measuring device for measuring the quantity and/or property of the predetermined component detected by the detecting section, and a container including a mechanism containing section for containing the puncture mechanism so that the needle point of the puncture mechanism can be moved by the drive means, and a sampling implement containing section for containing the body fluid sampling implement so that the body fluid sampling implement can be taken out.

The body fluid sampling unit is preferably adapted to be discarded after one time use in measuring the quantity and/or property of the predetermined component. Also, the sampling implement containing section extends from the mechanism containing section, and the sampling implement containing section and the mechanism containing section are disposed coaxially. The sampling implement containing section is preferably located on the side opposite to the direction of the needle point of the needle, with reference to the mechanism containing section. The direction in which the body fluid sampling implement is taken out is the same as the puncture direction of the needle.

The body fluid sampling implement is used by being taken out from the sampling implement containing section and being mounted to the component measuring device. The body fluid sampling implement is once mounted to the component measuring device in the state of being contained in the sampling implement containing section, and is thereafter released from the sampling implement containing section and mounted to the component measuring device by spacing the container away from the component measuring device.

The body fluid sampling implement is preferably tentatively fixed to the sampling implement containing section, and a force with which the sampling implement containing section fixes the body fluid sampling implement is smaller than a force of connection between the body fluid sampling implement and the component measuring device.

The puncture mechanism is preferably put into the state of being capable of an operation of puncturing the living body surface, by release of the body fluid sampling implement. The drive means includes a support section for supporting the needle, and a biasing section for biasing the support section, and a biasing force is accumulated in the biasing section by an operation of pressing the body fluid sampling implement against the component measuring device at the time of mounting the body fluid sampling implement to the component measuring device. In addition, the mechanism containing section includes an outer tube, the sampling implement containing section includes an inner tube which is slid inside the outer tube in its longitudinal direction and connected to the outer tube through the puncture mechanism, the body fluid sampling implement is mounted into the component measuring device by pushing, and when the operation of pushing the body fluid sampling implement into the component measuring device is conducted, the inner tube is pushed together with the body fluid sampling implement to move inside the outer tube, whereby a biasing force of the biasing section is accumulated.

The drive means includes a support section for supporting the needle, a biasing section for biasing the support section, and an operating member for displacing the support section so as to bias the biasing section.

The operating member can function as a cap for covering the needle point of the needle and maintaining a sterile state of the needle point. The mounted section has a bottomed tube shape, the introducing section protrudes in a tubular form to the outside from a bottom part of the mounted section, and the detecting section is disposed at the bottom part.

The detecting section includes a test paper carrying a reagent capable of a color reaction with the predetermined component in the body fluid. The detecting section includes at least two electrodes, and a reagent coated part coated with a reagent capable of reacting with the predetermined component in the body fluid to thereby generate a current between the electrodes. The sampling implement containing section has an opening permitting the body fluid sampling implement to be moved in and out therethrough, and has a seal member for sealing the opening in a gas-tight manner in the condition where the body fluid sampling implement is contained in the sampling implement containing section.

According to the disclosure here, the puncture mechanism and the body fluid sampling implement necessary for sampling a body fluid are contained in one case, so that the preparation for the sampling operation can be easily carried out, i.e., excellent operationality is attained in sampling a body fluid.

In the body fluid sampling unit described here, the body fluid sampling implement is contained in the case (container) including the puncture mechanism for sampling a body fluid. Therefore, preparation for body fluid sampling and body fluid component measurement can be easily carried out, i.e., the body fluid sampling unit is excellent in operationality in performing body fluid sampling and body fluid component measurement.

In addition, the body fluid sampling unit can be mounted to the component measuring device while keeping the body fluid sampling implement contained in the case. Therefore, it is unnecessary to take out the body fluid sampling implement from the case each time of use; thus, the body fluid sampling unit is excellent in operationality.

Also, the body fluid sampling unit is labor-saving in operation, since the puncture mechanism is charged and a stand-by condition for puncture is attained simultaneously with the mounting of the body fluid sampling implement to the component measuring device. After the puncture, the body fluid sampling (component measuring) operation can be speedily carried out, since the body fluid sampling implement has already been put into the state of being usable.

In addition, in the body fluid sampling unit, the puncture mechanism cannot be put into the stand-by state for puncture until the body fluid sampling implement is mounted to the component measuring device, i.e., until the body fluid sampling implement is separated from the body fluid sampling unit. Therefore, the sequence of operations such that puncture of a living body surface is conducted after the body fluid sampling implement is mounted to the component measuring device and the preparation for measurement is completed can be easily grasped.

Another aspect involves a method of obtaining a body fluid sample from a living body and using the body fluid sample. The method comprises removing a body fluid sampling implement from an interior of a container, wherein the body fluid sampling implement comprises a reagent containing part comprising a reagent adapted to interact with a predetermined component in the body fluid, and the interior of the container also containing a needle possessing a sharp needle point at a distal end of the needle. The method also involves mounting the body fluid sampling implement on a component measuring device which is adapted to measure a quantity and/or property of a predetermined component of the body fluid, wherein the body fluid sampling implement is removed from the interior of the container either before mounting the body fluid sampling implement on the component measuring device of after mounting the body fluid sampling implement on the component measuring device. Additionally, the method comprises puncturing a surface of the living body with the needle by moving the needle relative to the container to produce a body fluid, and introducing to the reagent containing part of the body fluid sampling implement the body fluid obtained by puncturing the surface of the living body with the needle so that the reagent interacts with the predetermined component in the body fluid.

BRIEF DESCRIPTION OF THE DRAWING FIGURES

Additional features and aspects of the body fluid sampling unit disclosed here will become more apparent from the following detailed description considered with reference to the accompanying drawing figures briefly described below in which like elements are designated by like reference numerals.

DETAILED DESCRIPTION

FIGS. 1-6 illustrate one embodiment of the body fluid sampling unit disclosed herein. In the description which follows, for purposes of convenience, the right side in FIGS. 1-6 (and in FIGS. 7-22 also) is referred to as "the proximal end", the left side is referred to as "the distal end", the upper side is referred to as "the upper side" or "upwards", and the lower side is referred to as "the lower side" or "downwards".

Figure 1:
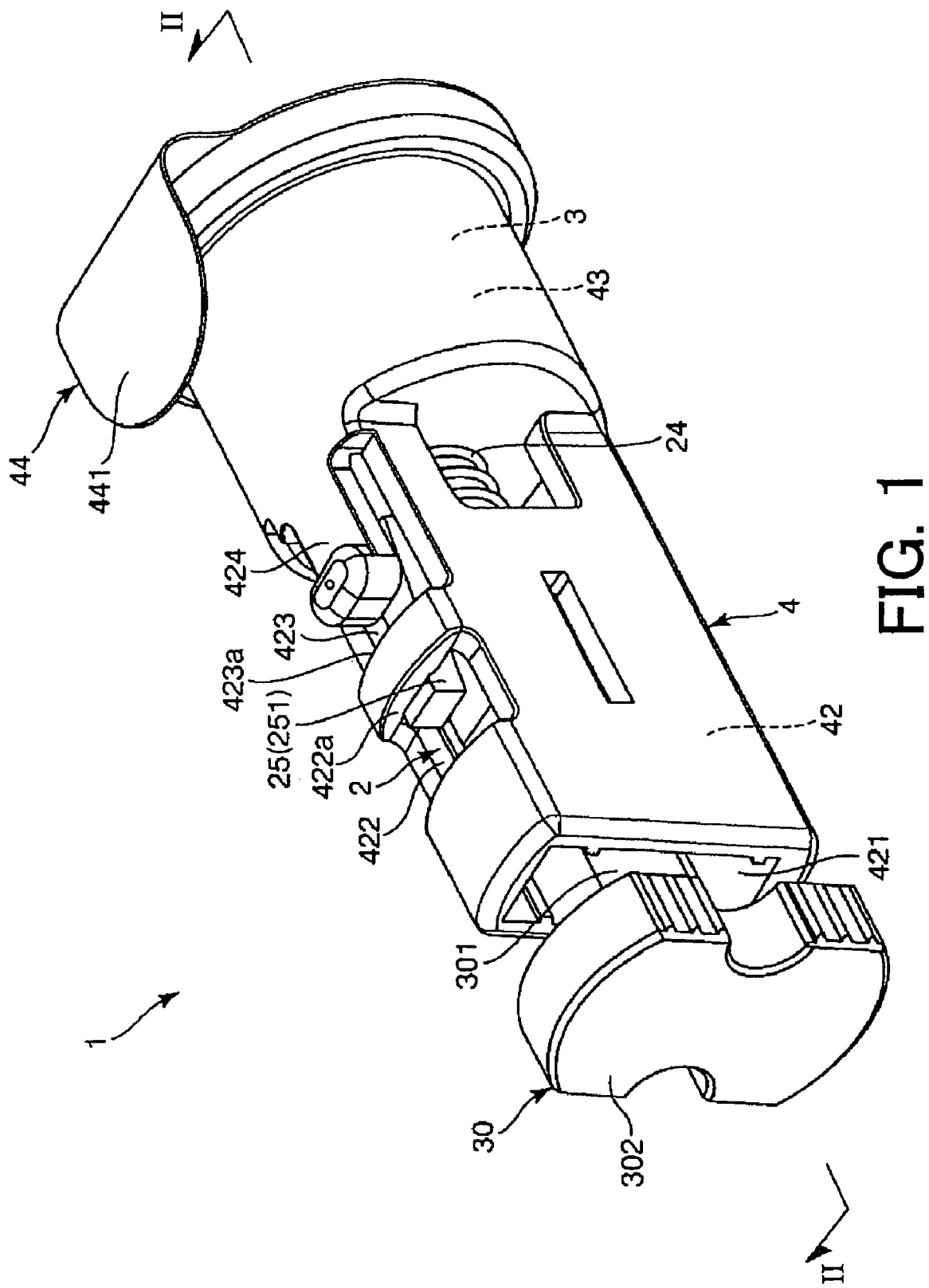
FIG. 1 is a perspective view of a first embodiment of the body fluid sampling unit disclosed herein.
Figure 2:
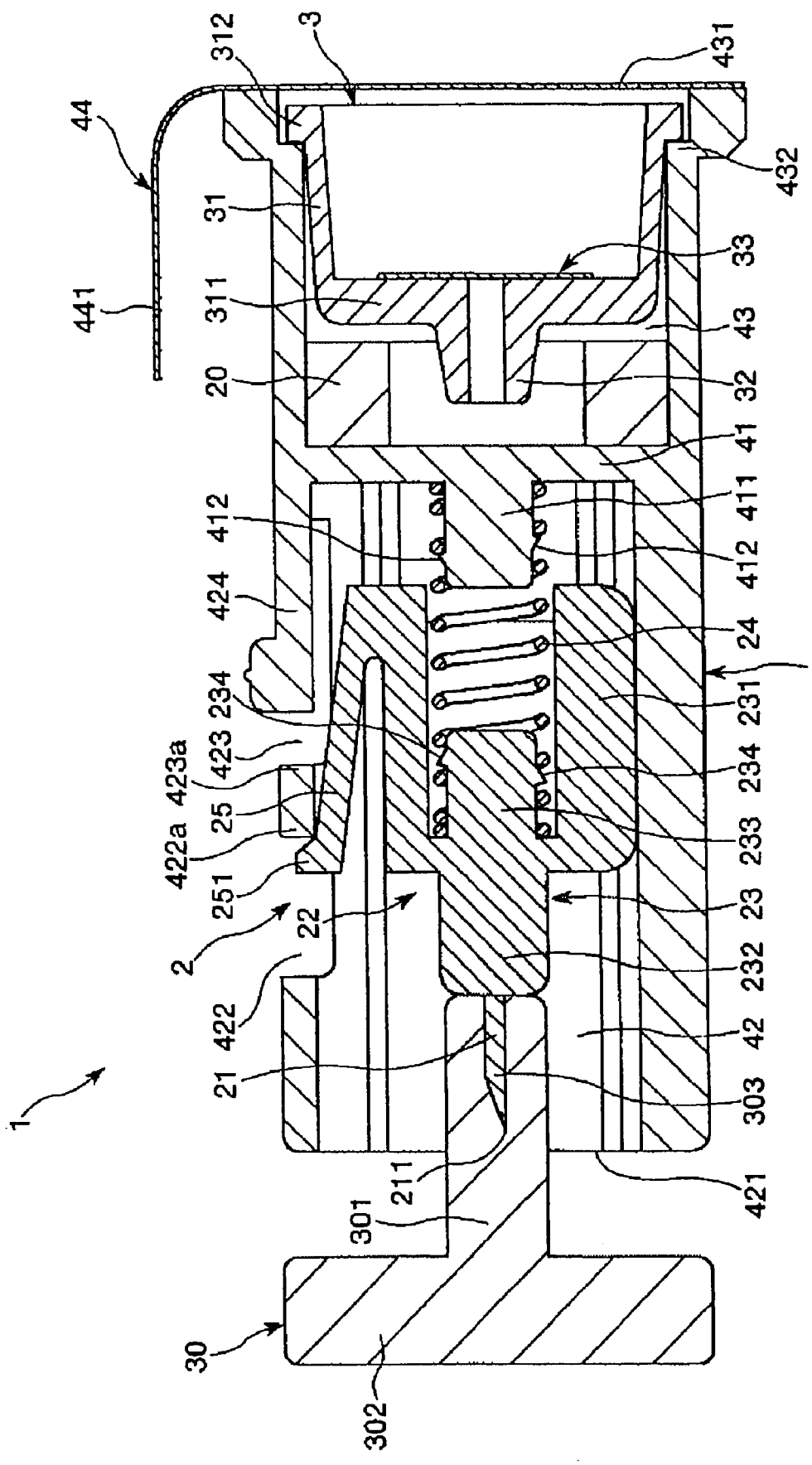
FIG. 2 is a longitudinal cross-sectional view of the body fluid sampling unit shown in FIG. 1 taken along the section line II-II in FIG. 1.

The body fluid sampling unit 1 shown in FIG. 1 and FIG. 2 includes a puncture mechanism 2, a tip (body fluid sampling implement) 3, and a case (casing or container) 4 containing the puncture mechanism 2 and the tip 3 collectively therein. The puncture mechanism 2 is configured to puncture a living body surface (skin). In addition, the tip 3 is configured to sample body fluid obtained from a puncture portion of the living body surface punctured by the puncture mechanism 2. The tip 3 is used in the state of being mounted to a component measuring device 100 for measuring the quantity and/or property of a predetermined component in the body fluid.

The body fluid sampling portion of the living body surface (skin) from which a body fluid sample is obtained is preferably a finger, but may be other portions, for example a hand (the palm, the back of a hand, the side portion of a hand), an arm, a thigh, an earlobe, or the like. The following description describes, as an example, blood as the body fluid, blood glucose as the predetermined component, and a fingertip (finger) as the body fluid sampling portion of the living body.

As shown in FIGS. 2-5, the case 4 is composed of a tubular body. The case 4 is provided with a partition wall 41 partitioning the inner cavity or interior (hollow section) of the case 4 into a mechanism containing section 42 located on the distal end side, and a sampling implement containing section 43 located on the proximal end side.

The case 4 can be said to include the mechanism containing section 42 possessing a bottomed tube shape, and the sampling implement containing section 43 (extension section) extending (projecting in a tubular form) from the bottom part of the mechanism containing section 42 toward the proximal end side.

In the illustrated embodiment, the case 4 is configured so that the mechanism containing section 42 and the sampling implement containing section 43 are positioned coaxially. This helps ensure that, at the time of using the body fluid sampling unit 1, the operator can easily recognize or understand the position at which the needle point 211 protrudes and the position where blood is spotted, which is advantageous in that a puncture at a unintended position and/or a failure in realizing the spot-like deposition of blood can be inhibited or prevented.

One puncture mechanism 2 is contained in the mechanism containing section 42 of the case 4, and one tip 3 is contained in the sampling implement containing section 43 of the case 4. The body fluid sampling unit 1 is thus relatively small in size and suitable, for example, for carrying the body fluid sampling unit 1. In addition, compared to needing to prepare four articles or parts as in known devices, only two articles need to be prepared. This helps facilitate handling and allows relatively easy measurement in a limited space, thus advantageously lessening the burden on the operator.

Figure 4:
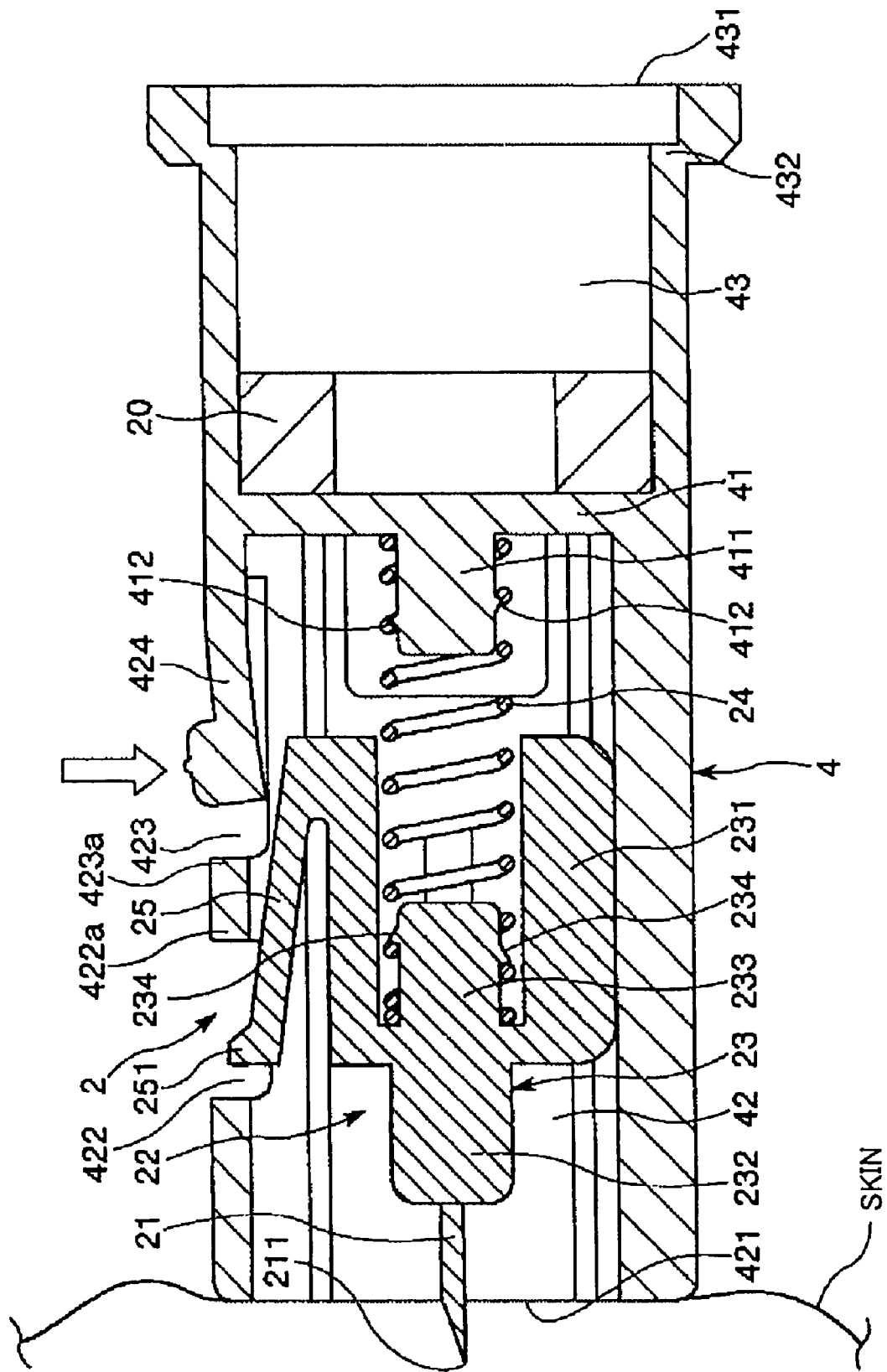
FIG. 4 is a longitudinal cross-sectional view of the body fluid sampling unit showing another operating condition of the body fluid sampling unit during use.

The mechanism containing section 42 has a distal end opening 421 which opens at the distal end of the mechanism containing section 42 (the case 4) on the side opposite the partition wall 41. As shown in FIG. 4, the distal end opening 421 functions as a protrusion opening through which the needle point 211 of the puncture mechanism 2 protrudes at the time of puncture of a fingertip.

In addition, the mechanism containing section 42 has a first opening (first engaging part) 422 and a second opening (second engaging part) 423 where upper-side parts of the wall of the case 4 are provided with through openings. The second opening 423 is disposed on the proximal end side of the first opening 422.

Figure 3:
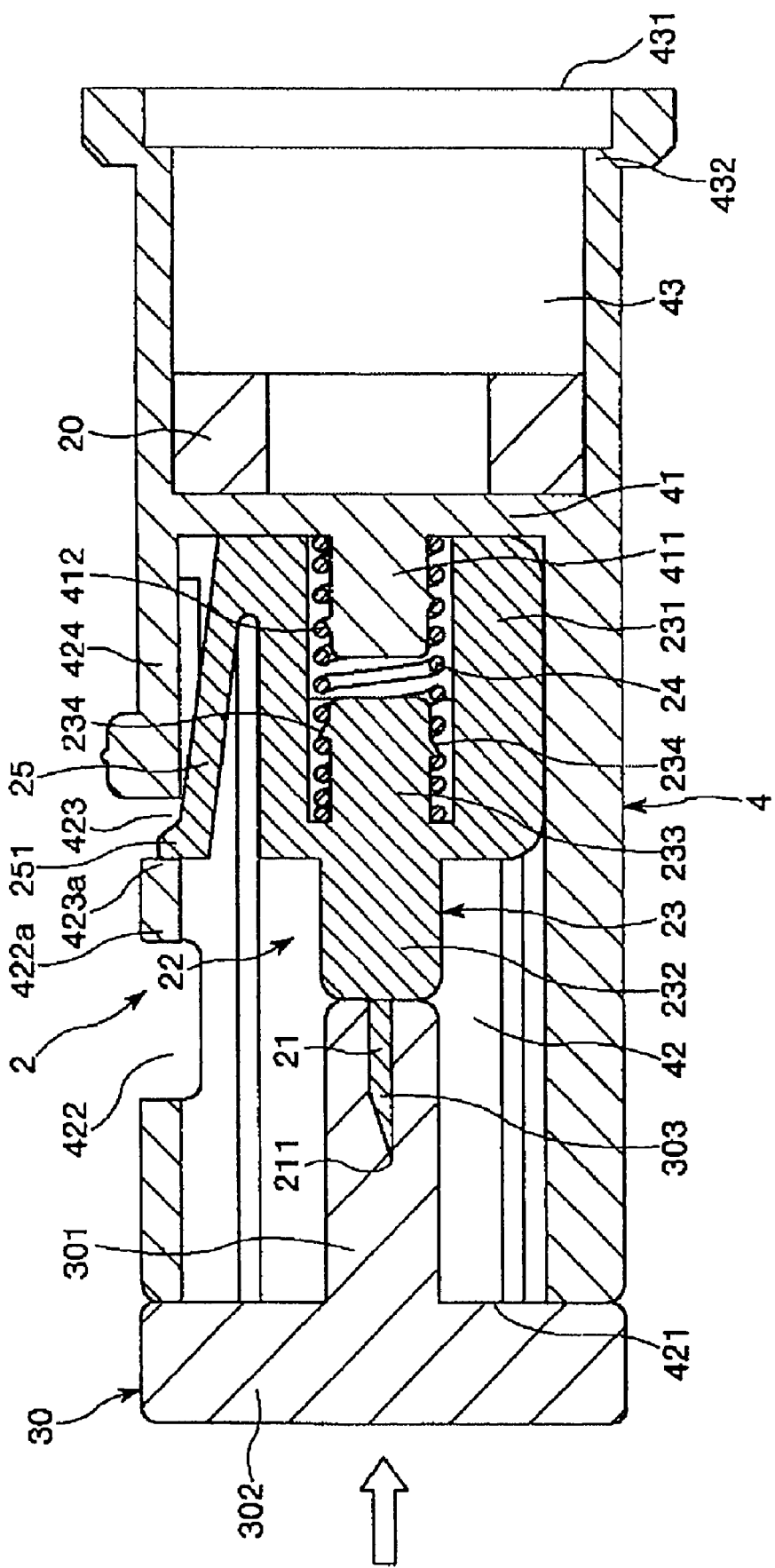
FIG. 3 is a longitudinal cross-sectional view of the body fluid sampling unit showing an operating condition of the body fluid sampling unit during use.

The first opening 422 is roughly quadrangular in shape when viewed from the upper side. In addition, the second opening 423 is U-shaped when viewed from the upper side. As shown in FIGS. 2, 3 and 4, an engaging piece 25 associated with the puncture mechanism 2 engages either the first opening 422 or the second opening 423 according to the operating condition of the puncture mechanism 2.

A plate piece (tongue piece) 424 supported at its proximal end is formed on the inside of the second opening 423. The plate piece 424 ensures that the engaging piece 25 can be disengaged from the second opening 423 by depressing downward a distal end part of the plate piece 424 in the condition where the engaging piece 25 is in engagement with the second opening 423 (see FIGS. 3 and 4). Therefore, the plate piece 424 serves as an operating section for disengaging the engaging piece 25 from the second opening 423.

As shown in FIG. 2, the sampling implement containing section 43 which is adapted to contain the tip 3 is located on the proximal end side (on the side opposite to the protrusion direction of the needle point 211) of the mechanism containing section 42.

The sampling implement containing section 43 has a proximal end opening 431 opening at the proximal end of the sampling implement containing section 43 (the case 4). Through the proximal end opening 431, the tip 3 can be contained (inserted) into the sampling implement containing section 43, and the tip 3 contained in the sampling implement containing section 43 can be taken out.

In addition, a membrane member (seal member) 44 for covering the proximal end opening 431 is fixed to the proximal end opening 431 preliminarily (in the unused state of the body fluid sampling unit 1). The method of fixing in this case is not particularly limited; for example, the fixation may be made by adhesion (adhesion with an adhesive or by use of a solvent).

The membrane member 44 is for sealing the proximal end opening 431 in a gas-tight manner. This makes it possible to maintain the cleanliness of the tip 3 contained in the sampling implement containing section 43. Therefore, the membrane member 44 has the function as a state maintaining means for maintaining the clean state of the tip 3. In addition, the membrane member 44 can prevent the tip 3 contained in the sampling implement containing section 43 from deteriorating with time due to moisture absorption. Therefore, the membrane member 44 has also the function as a moisture proofing means for the tip 3.

The membrane member 44 is peeled (released) from the proximal end opening 431 at the time of taking out the tip 3 containing in the sampling implement containing section 43. At the time of peeling the membrane member 44, the operation (peeling operation) can be easily carried out by gripping (pinching) a tab (edge part) 441 of the membrane member 44.

In addition, the sampling implement containing section 43 has a stepped part 432 varied in inside diameter (enlarged in diameter), on the distal end side and in the vicinity of the proximal end opening 431. As shown in FIG. 2, the tip 3 contained in the sampling implement containing section 43 has a part (flange part 312) thereof in abutment on the stepped part 432. This makes it possible to prevent the tip 3 from being inserted excessively into the sampling implement containing section 43 and, therefore, to easily take out the tip 3 contained in the sampling implement containing section 43.

The material constituting the case 4 as above is not particularly limited, and, for example, a resin material can be used. Examples of the resin material which can be used include thermoplastic resins ordinarily used in injection molding, such as ABS resin, AS resin, polyethylene, polypropylene, polystyrene, polyvinyl chloride, polyvinylidene chloride resin, polyphenylene oxide, thermoplastic polyurethane, polymethylene methacrylate, polyoxythylene, fluororesin, polycarbonate, polyamide, acetal resin, acrylic resin, polyethylene terephthalate, etc.; and thermosetting resins such as phenolic resin, epoxy resin, silicone resin, unsaturated polyester, etc.

Besides, a desiccant agent 20 is contained in the sampling implement containing section 43, together with the tip 3. The drying agent 20 has the function of preventing moisture absorption of the tip 3 in the sampling implement containing section 43, i.e., the function of maintaining the dry state of a test paper 33.

The drying agent 20 is ring-like in outer shape, and is disposed concentrically with the sampling implement containing section 43. In addition, the drying agent 20 may be fixed to or may not be fixed to the sampling implement containing section 43.

As the drying agent 20, various drying agents can be used. A preferable example of the drying agent 20 is composed of at least one selected from the group consisting of silica, alumina, synthetic zeolites such as Molecular Sieves, etc., natural zeolites such as mordenite, erionite, etc., chlorides of alkaline earth metals such as calcium chloride, magnesium chloride, etc., and clay minerals such as pearlite, activated white clay, etc.

As above-mentioned, one puncture mechanism 2 is contained in the mechanism containing section 42. The puncture mechanism 2 includes a needle 21, and a drive means (drive mechanism) 22 for moving the needle 21.

The needle 21 is composed, for example, of a long solid member (or hollow member) formed of a metallic material such as stainless steel, aluminum, aluminum alloy, titanium, titanium alloy, etc., and is provided at its distal end with a sharp needle point (blade edge) 211. The needle point 211 is used to puncture the surface (skin) of a fingertip.

The drive means 22 includes a support section 23 for supporting the needle 21, a coil spring (biasing section) 24 for biasing the support section 23, and the engaging piece 25 capable of engaging with the first opening 422 and the second opening 423 of the case 4.

The support section 23 can be displaced into any of an initial position (the state shown in FIGS. 2 and 5), a stand-by position (the state shown in FIG. 3), and a puncture position (the state shown in FIG. 4). The "initial position" means a position where a biasing force of the coil spring 24 does not act on the support section 23. In addition, the "stand-by position" means a position where the biasing force is accumulated in the coil spring 24 and preparation for puncture of a fingertip by the needle 21 is made. Further, the "puncture position" means a position where puncture by the needle 21 (needle point 211) is conducted.

The support section 23 includes a body part 231 angular U shaped in longitudinal sectional shape, a distal end projected part 232 projectingly formed at the distal end of the body part 231, and a proximal end projected part 233 projectingly formed on the inside of the body part 231.

The body part 231 is disposed in the mechanism containing section 42 so that the opening (opened) side (the opening side of the angular U shape) thereof is disposed on the proximal end side. In addition, the body part 231 can be slid inside the mechanism containing section 42 along the longitudinal direction thereof, by the biasing force of the coil spring 24.

The distal end projected part 232 projected in the direction of the distal end is provided on the side, opposite to the angular U-shaped opening side, of the body part 231. The distal end projected part 232 is cylindrical in outer shape. The needle 21 is supported by (fixed to) the distal end projected part 232, concentrically with the tip distal end projected part 232.

In addition, the body part 231 is provided, on the opposite side of the distal end projected part 232, with the proximal end projected part 233 projected in the direction of the proximal end. The proximal end projected part 233 is cylindrical in outer shape. A distal end section of the coil spring 24 is fitted over the proximal end projected part 233.

The proximal end projected part 233 is provided at its outer peripheral part with a plurality of pawl parts 234 projecting in the outer radial direction. Each of the pawl parts 234 is wedge-shaped so that its height gradually increases as one goes toward the distal end. Each of the pawl parts 234 is engagement with the distal end section of the coil spring 24. This prevents the proximal end projected part 233 from slipping off the distal end section of the coil spring 24, i.e., this makes it possible to support and fix the distal end section of the coil spring 24.

In addition, a proximal end section of the coil spring 24 is supported by a projected part 411 projectingly formed at the partition wall 41 of the case 4. The projected part 411 is opposed to the proximal end projected part 233, and is formed at the partition wall 41 of the case in the form of projecting in the direction of the distal end. The projected part 411 is cylindrical in outer shape. A proximal end section of the coil spring 24 is fitted over the projected part 411.

The projected part 411 is provided at its outer peripheral part with a plurality of pawl parts 412 projecting in the outer radial direction. Each of the pawl parts 412 is wedge-shaped so that its height gradually increases as one goes toward the proximal end. Each of the pawl parts 412 is in engagement with the proximal end section of the coil spring 24. This prevents the projected part 411 from slipping off the proximal end section of the coil spring 24, i.e., this makes it possible to support and fix the proximal end section of the coil spring 24.

At a proximal end part of the body part 231, the engaging piece 25 cantilever supported by the proximal end part is formed as one body with the body part 231. Of the engaging piece 25, the proximal end is a fixed end supported by the body part 231, and the distal end is a free end. The engaging piece 25 is an elastic piece having elasticity.

The engaging piece 25 is provided with a lock part (engaging part) 251 on the free end side. The lock part 251 is a portion having an upwardly projecting block-like shape.

The material constituting the support section 23 (inclusive of the engaging piece 25) is not particularly limited. For example, materials similar to those which can be used to form the case 4 can be used to fabricate the support section 23.

In addition, the material constituting the coil spring 24 is not limited to a specific material. Examples of materials which can be used individually or in combination include various metallic materials, various plastics and the like.

The operation of the puncture mechanism 2 configured in the manner described above is as follows.

As shown in FIG. 2, when the support section 23 is in its initial position, i.e., when the puncture mechanism 2 is in an unused state, the coil spring 24 has a natural length. This prevents the needle 21 (support section 23) from unintended movement so that accidental sticking by the needle point 211 due to movement of the needle 21 can be relatively reliably prevented.

In addition, the needle 21 is covered by an operating member (cap) 30 which will be described later. This cap 30 can help prevent accidental sticking by the needle point 211 from occurring.

The engaging piece 25 has its lock part 251 locked to a proximal end part 422a of the first opening 422. This maintains the support section 23 in the stand-by position, i.e., this can prevent the support section 23 from unintended movement (e.g., toward the proximal end side).

When the support section 23 is pushed in the direction of the proximal end starting from the condition shown in FIG. 2, the lock part 251 of the engaging piece 25 comes over the proximal end part 422a of the first opening 422, against the elastic force (biasing force) of the engaging piece 25. Attendant on the pushing operation applied to the support section 23, the lock part 251 is moved further in the direction of the proximal end, is brought into the second opening 423, and is engaged with a distal end part 423a of the second opening 423 (see FIG. 3). In addition, an upper surface of the engaging piece 25 comes into contact with the distal end of the plate piece 424.

At this time, the proximal end of the body part 231 of the support section 23 abuts on the partition wall 41. As a result, the movement of the support section 23 in the proximal end direction end is stopped.

In addition, the coil spring 24 is compressed (contracts) since the spacing between the body part 231 of the support section 23 and the partition wall 41 is reduced. As a result, a biasing force is accumulated in the coil spring 24.

With the operation described above starting from the initial position, the support section 23 is displaced into the stand-by position, i.e., the puncture mechanism 2 (body fluid sampling unit 1) is put into the state shown in FIG. 3. When the puncture mechanism 2 is brought into the state shown in FIG. 3, the operating member 30 is detached from the puncture mechanism 2.

When the plate piece 424 is depressed downward against the biasing force of the engaging piece 25 starting from the condition shown in FIG. 3, the lock part 251 of the engaging piece 25 and the distal end part 423a of the second opening 423 are disengaged from each other. At this time, the compressed state of the coil spring 24 is cleared, and the coil spring 24 extends in the direction of the distal end. This displaces the support section 23 into the puncture position so that the needle point 211 protrudes from the distal end opening 421, i.e., the puncture of a fingertip is enabled as shown in FIG. 4.

Figure 5:
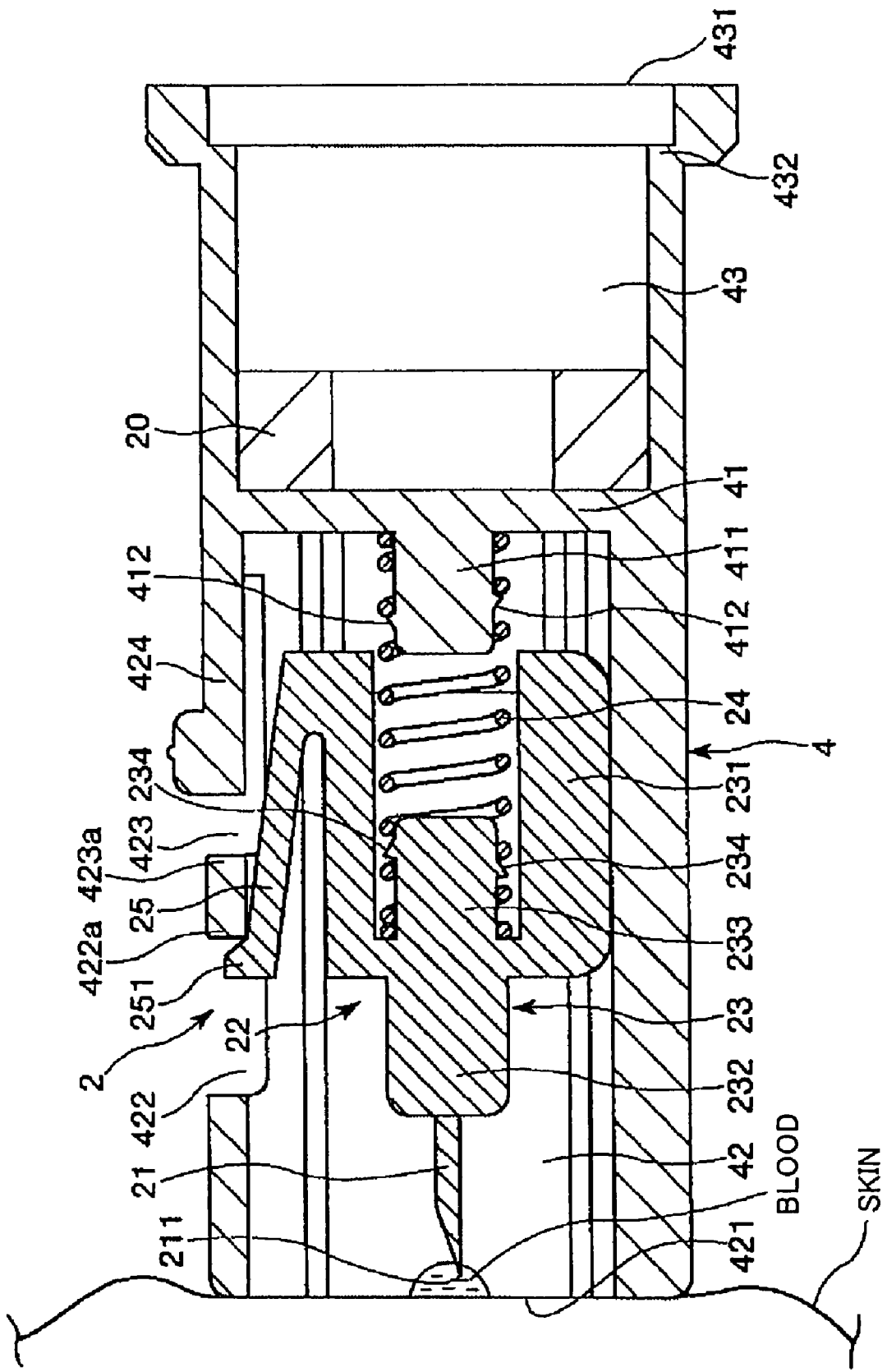
FIG. 5 is a longitudinal cross-sectional view of the body fluid sampling unit showing another operating condition of the body fluid sampling unit during use.

Thereafter, the coil spring 24 returns to the natural length, so that the support section 23 is returned to the initial position as seen in FIG. 5.

At this time, the needle point 211 of the needle 21 is not protruding from the distal end opening 421. That is, upon returning to the initial position shown in FIG. 5, the needle point 211 is located inside the mechanism containing section 42. By virtue of this, accidental sticking by the needle point 211 can be prevented.

With the operation of the puncture mechanism 2 described above, the needle 21 (support section 23) is relatively reliably displaced to be located in the initial position, the stand-by position, the puncture position and the initial position, in this order. The puncture of the fingertip can thus be carried out relatively assuredly. In addition, the position of the needle 21 can be grasped (recognized) according to the position of the engaging piece 25 relative to the case 4, so that it is possible to perform a safe puncture operation, namely, to prevent accidental sticking.

Thus, the body fluid sampling unit 1 possesses excellent operational characteristics in sampling blood by puncture of a fingertip.

As shown in FIGS. 1-3, the operating member or cap 30 is detachably mounted to the puncture mechanism 2 (support section 23). The operating member 30 is so configured that in the condition where it is mounted to the support section 23, the support section 23 can be displaced from the initial position into the stand-by position, i.e., the support section 23 can be operated, by use of the operating member 30.

The operating member 30 includes a connection section 301 to be connected to the support section 23, and a grip section 302 formed at a distal end part of the connection section 301.

The grip section 302 is a portion which is gripped at the time of operating the operating member 30. The grip section 302 is plate-like in shape.

The connection section 301 is a portion which is cylindrical in outer shape. The connection section 301 is formed at the proximal end face of the grip section 302 so that the connection section 301 and the grip section 302 are integrally formed as a unitary one-piece body.

By pushing the operating member 30 in the proximal direction, the support section 23 can be displaced or moved from the initial position to the stand-by position relatively easily and assuredly.

In addition, the operating member 30 is detached (released) from the support section 23 when its operation is completed, i.e., when the support section 23 is displaced from the initial position into the stand-by position. This makes it possible to prevent the operating member 30 from obstructing the subsequent operation of the body fluid sampling unit 1, i.e., the puncture operation applied to the fingertip.

In addition, the connection section 301 is provided with a needle containing section 303 composed of a hollow section opening at the proximal end. In the condition where the operating member 30 is mounted to the support section 23, the needle 21 as a whole is contained in (covered by) the needle containing section 303. This helps maintain the sterile state of the needle 21. Therefore, the operating member 30 (needle containing section 303) functions also as a state maintaining means (cap) for maintaining the sterile state of the needle 21. In addition, since the needle 21 is entirely contained, accidental sticking by the needle point 211 can be prevented securely.

Examples of the material constituting the operating member 30 include, for example, materials similar to those which can be used to form the case 4 as mentioned above.

As shown in FIG. 2, where the body fluid sampling unit 1 is in the unused state, the tip 3 is contained in the sampling implement containing section 43. At the time of sampling blood by use of the tip 3, the tip 3 is taken out of the sampling implement containing section 43 and mounted to the component measuring device 100 as shown in FIG. 6.

Figure 6:
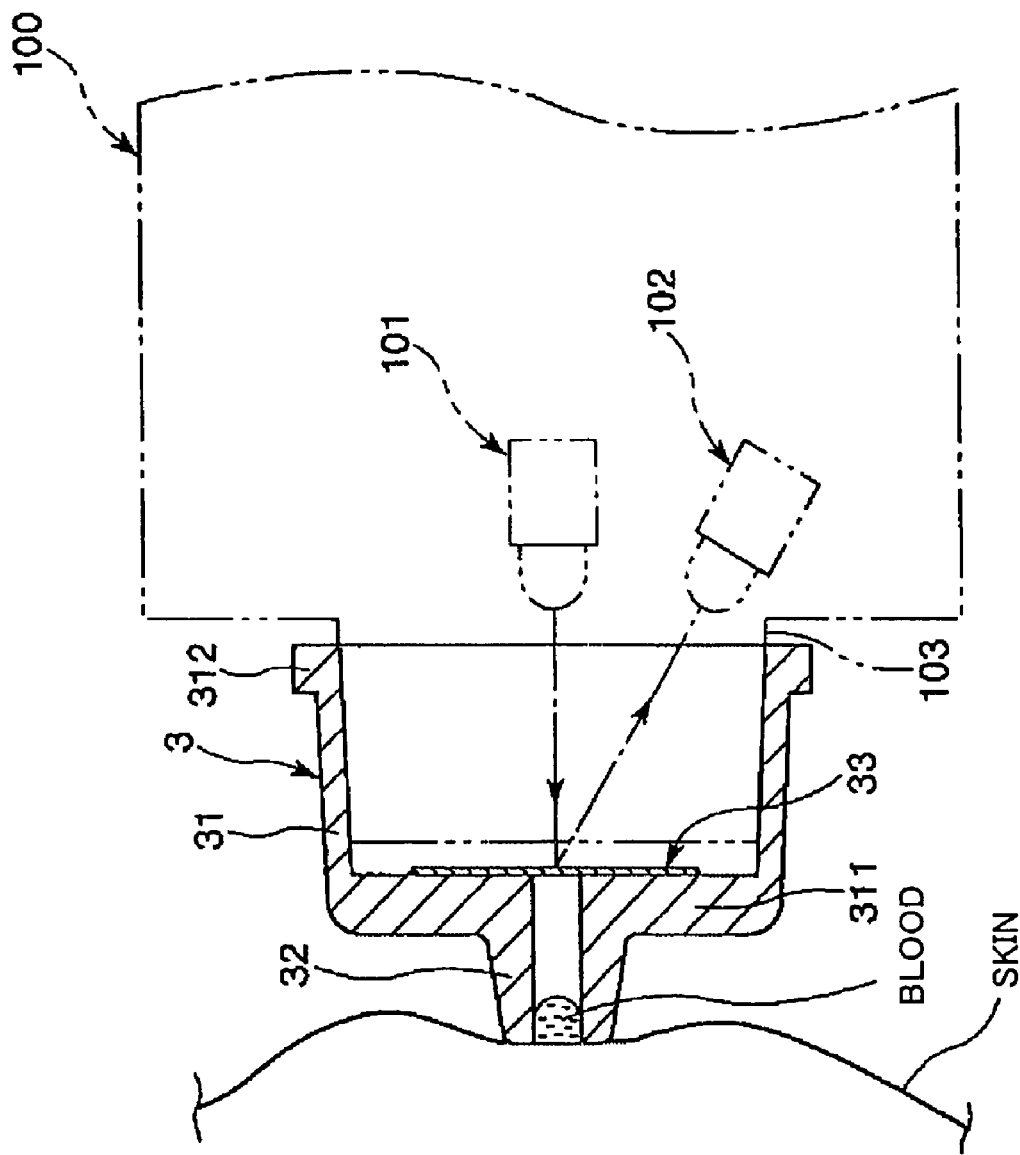
FIG. 6 is a longitudinal cross-sectional view of the body fluid sampling unit showing another operating condition of the body fluid sampling unit during use.
Figure 7:
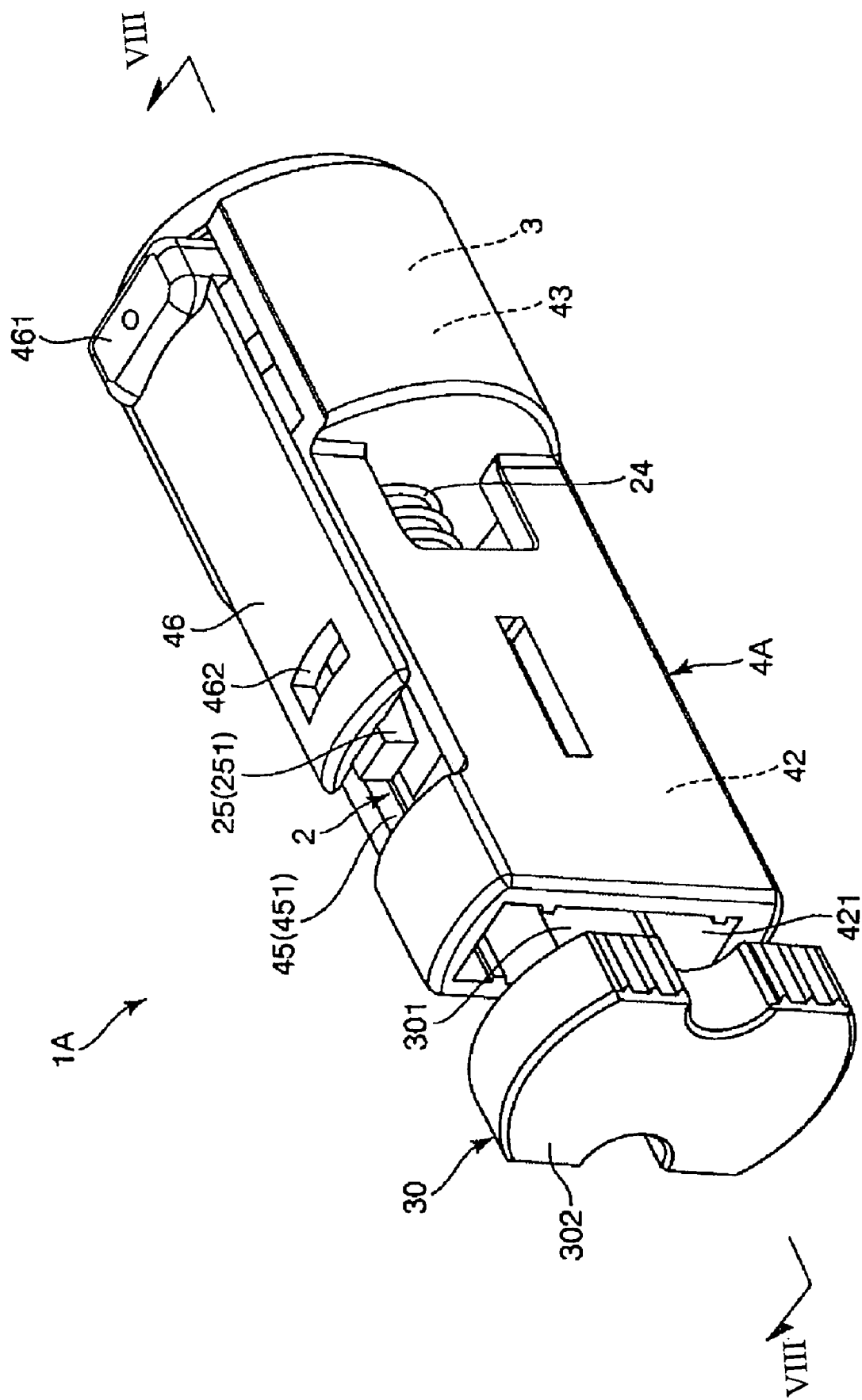
FIG. 7 is a perspective view of a second embodiment of the body fluid sampling unit.

As shown in FIGS. 2 and 6, the tip 3 includes a tip body (mounted section) 31, an introducing section 32 projectingly formed at the tip body 31, and a test paper 33 as a detecting section disposed in the tip body 31.

The tip body 31 is a portion to be mounted to the component measuring device 100 (see FIG. 6). The tip body 31 has a bottomed cylindrical shape. In the condition where the tip body 31 (tip 3) is mounted to the component measuring device 100, the inner peripheral part of the tip body 31 and the outer peripheral part of a tip mounting section 103 of the component measuring device 100 to be described later are fitted to or engaged with each other as shown in FIG. 6.

In addition, the outer peripheral part of the tip body 31 is provided near its proximal end part with a flange part 312 steeply enlarged in outside diameter. As mentioned previously, in the condition where the tip 3 is contained in the sampling implement containing section 43, the flange part 312 abuts on the stepped part 432 of the sampling implement containing section 43.

The introducing section 32 is a portion for introducing to the test paper 33 the blood flowing out from the puncture portion of a skin punctured by the needle point 211. The introducing section 32 is provided at a bottom part 311 of the tip body 31, and is composed of a tubular body projecting in the direction of the distal end (outwards). Blood passes through a hollow section or through hole of the tubular body.

The test paper 33 is disposed on the proximal end side of the bottom part 311 of the tip body 31. The test paper 33 is a reagent carrying part of the tip 3 which carries a reagent capable of a color reaction with glucose in blood. By this, the glucose in the blood introduced through the introducing section 32 is detected.

The test paper 33 has the reagent (coloring reagent) carried by (impregnating) a carrier capable of absorbing blood. The carrier is preferably composed of a porous sheet.

The use of the carrier composed of a porous sheet helps ensure that, in the case where the reagent with which to impregnate the carrier is a reagent system involving a process of using oxygen such as an oxidase reaction, sufficient supply of oxygen from the atmospheric air is secured after blood is spread on the test paper 33 so that the reaction can be made to proceed swiftly. Therefore, the coloring condition can be detected without removal of the blood or a filtered component thereof (red blood cell, etc.).

Examples of the carrier composed of a porous sheet include non-woven fabric, woven fabric, stretched sheet, membrane filter, and filter paper. Examples of the material constituting the carrier include polyesters, polyamides, polyolefins, polysulfones, celluloses, silicates, and fluororesins. Specific examples of the material include polyethylene terephthalate, polybutylene terephthalate, polyether-sulfone, nitrocellulose, cellulose, glass, and polytetrafluoroethylene (Teflon (registered trademark)).

The material constituting the carrier is preferably a material produced in the state of being impregnated with an aqueous solution with the reagent dissolved therein, or is a hydrophilic material or a material treated to be hydrophilic so as to ensure speedy absorption and spreading of blood.

In the case of measurement of blood glucose level, examples of the reagent carried by the test paper 33 include glucose oxidase (GOD), peroxidase (POD), and chromogenic agents (coloring reagents) such as 4-aminoantipyrine, N-ethyl-N-(2-hydroxy-3-sulfopropyl)-m-toluidine. Other than these, examples of the reagent include those capable of reacting with blood component, such as ascorbic acid oxidase, alcohol oxidase, cholesterol oxidase, etc. and the same chromogenic agents (coloring reagents) as above, according to the component to be measured. Further, a buffer such as a phosphoric acid buffer may be contained in the reagent. Incidentally, the kinds and components of the reagent are naturally not limited to these.

By way of example, the tip 3 can be made of materials similar to those which can be used to form the case 4 as discussed above.

As described above, the tip 3 is used by being taken out from the sampling implement containing section 43 and mounted to the component measuring device 100. The component measuring device 100 to which the tip 3 is mounted is described below.

As shown in FIG. 6, the component measuring device 100 has a tubular tip mounting section 103 to which the tip 3 is detachably mounted. A light emitting element (light emitting diode) 101 and a light receiving element (photo-diode) 102 are provided in the vicinity of the proximal end of the tip mounting section 103. The light emitting element 101 emits pulsed light at a predetermined time interval, for example.

In addition, the component measuring device 100 has a control means (not shown) composed of a micro-computer. The control means incorporates an arithmetic unit for computing the glucose content based on a signal from the light receiving element 102.

The component measuring device 100 is configured to perform measurement after the tip 3 is mounted to the tip mounting section 103 and blood is supplied to the test paper 33 in the tip 3.

In other words, first, with the light emitting element 101 in the component measuring device 100 turned ON, light emitted from the light emitting element 101 is radiated onto the test paper 33 in the tip 3, whereby reflected light is obtained. The intensity of the reflected light corresponds to the intensity of coloring of the test paper 33, i.e., to the quantity (concentration) of glucose in the blood. The reflected light is received by the light receiving element 102 where it undergoes photoelectric conversion. An analog signal corresponding to the quantity of light received is outputted from the light receiving element 102, the analog signal is converted into a digital signal, which is inputted to the control means where desired arithmetic processing, correction processing and the like are conducted, and the quantity of glucose in the blood is quantized (blood glucose level is determined).

The tip 3 is contained in the sampling implement containing section 43 when the body fluid sampling unit 1 is in the unused state. The tip 3 in this instance is tentatively fixed to, or contained in, the sampling implement containing section 43. Here, the expression "tentatively fixed" means the condition where the tip 3 is prevented from being involuntarily released from the sampling implement containing section 43 and where the tip 3 can be taken out as required.

With the tip 3 thus tentatively fixed and contained in the sampling implement containing section 43, an outer peripheral part of the tip 3 and an inner peripheral part of the sampling implement containing section 43 are fitted to each other as shown in FIG. 2. The fitting force (fixing force) exerted on the tip 3 from the sampling implement containing section 43 is set to be smaller than the fitting force (connecting force) exerted on the tip 3 by the component measuring device 100 (the tip mounting section 103).

In addition, in order to take out the tip 3 thus tentatively fixed, the tip mounting section 103 of the component measuring device 100 is pushed into the tip body 31 to once fit (connect) them to each other, and thereafter the case 4 is pulled (spaced away) in the direction of the distal end relative to the component measuring device 100. The tip 3 is thus securely taken out (released) in the direction of the proximal end from the sampling implement containing section 43, and is assuredly mounted to the component measuring device 100.

Thus, in the body fluid sampling unit 1, the operation in which the tip 3 is mounted to the component measuring device 100 is utilized also as the operation in which the tip 3 is taken out from the sampling implement containing section 43. The unit thus possesses excellent operational aspects.

The tip body 31 is tubular (bottomed cylindrical) in shape. Therefore, when the dimensional tolerance associated with fitting the tip body 31 and the sampling implement containing section 43 is appropriately set, the fitting force therebetween can be easily modified to a desired magnitude. In addition, when the dimensional tolerance in fitting the tip body 31 and the tip mounting section 103 is appropriately set, the fitting force therebetween can be relatively easily modified to a desired magnitude.

By virtue of this, the relationship in magnitude between the former fitting force (fitting force between the tip body 31 and the sampling implement containing section 4) and the latter fitting force (fitting force between the tip body 31 and the tip mounting section 103) can be assuredly set so as to satisfy the relationship of [the former fitting force]<[the latter fitting force]. Therefore, the tip 3 can be taken out from the sampling implement containing section 43 more securely and reliably, and can be mounted to the component measuring device 100 more assuredly.

A method of using the body fluid sampling unit 1 (i.e., the method of sampling blood and measuring the blood glucose level of the blood by use of the body fluid sampling unit 1) is as follows.

First, the body fluid sampling unit 1 is prepared in the manner shown in FIGS. 1 and 2. The body fluid sampling unit 1 contains one puncture mechanism 2 for puncturing a fingertip and one tip 3 for sampling blood from the puncture portion which are necessary for measurement of blood glucose level. Therefore, preparation for measurement of blood glucose level is relatively easy to carry out.

Next, the tab 441 of the membrane member 44 is gripped and the membrane member 44 is peeled off. Then, as mentioned above, the tip 3 contained in the sampling implement containing section 43 is pushed into the component measuring device 100 to connect them, whereby the tip 3 is mounted to the component measuring device 100. The operation of mounting the tip 3 is thus relatively easy to carry out.

Subsequently, the operating member 30 is pushed relative to the body fluid sampling unit 1 from which the tip 3 has been taken out, whereby the support section 23 of the puncture mechanism 2 is displaced from the initial position into the stand-by position (see FIG. 3).

Next, the operating member 30 in which the needle point 21 is sealed is taken off (e.g., by twisting), and the distal end opening 421 of the case 4 is brought into contact with the fingertip. In this condition, the plate piece 424 is depressed downward. This displaces the support section 23 from the stand-by position into the puncture position, whereby puncture of the fingertip is effected as shown in FIG. 4. By this, puncture of the fingertip by the puncture implement 3 is achieved, and a minute amount (for example, 1 µL or less) of blood flows out (is discharged) from the puncture portion onto the skin. The support section 23 thereafter returns to the initial position as indicated in FIG. 5.

Subsequently, the body fluid sampling unit 1 from which the tip 3 has been taken out is spaced away from the puncture portion (fingertip), and the introducing section 32 of the tip 3 mounted to the component measuring device 100 is brought into contact with the puncture portion (blood). The blood at the fingertip passes through the introducing section 32 by capillary action and is supplied to the test paper 33, for example so that the blood spreads on the test paper 33.

Attendant on the supply of the blood onto the test paper 33, glucose in the blood and the reagent carried by the test paper 33 react with each other, resulting in coloring of the test paper 33 according to the quantity of glucose.

The intensity of coloring of the test paper 33 is optically measured by the component measuring device 100 as above-mentioned, whereby the quantity of glucose in the blood (blood glucose level) is determined.

After the measurement is finished, the tip 3 is detached from the tip mounting section 103. The used tip 3 thus detached is discarded. In discarding the used tip 3, the tip 3 may be again contained into the sample implement containing section 43 and discarded together with the puncture mechanism 2. This makes it possible to prevent contamination with the blood adhering to (remaining in or on) the tip 3.

Thus, in the body fluid sampling unit 1, the puncture mechanism 2 is brought into puncture of the fingertip in the condition where the tip 3 is released. This makes it possible to recognize the use of the tip 3 after the puncturing operation, and to relatively easily grasp (understand) the sequence of operations of the body fluid sampling unit 1. This is extremely effective, for example, for a beginner with respect to the use of the body fluid sampling unit 1. In other words, the beginner who uses the body fluid sampling unit 1 for the first time can correctly operate (use) the body fluid sampling unit 1.

In addition, the body fluid sampling unit 1 is used in relation to the puncture portion punctured by the puncture mechanism 2 so that the blood discharged from the (same) puncture portion is sampled by the tip 3. With the body fluid sampling unit 1 used in this manner, the sequence of operations of the body fluid sampling unit 1 can be easily grasped. Therefore, the body fluid sampling unit 1 is excellent in operationality.

In addition, after the puncture, the blood sampling operation (blood glucose level measuring operation) can be relatively speedily carried out since the tip 3 has already been put into a usable state, i.e., the tip 3 has already been mounted to the component measuring device 100.

In addition, in the body fluid sampling unit 1, the direction in which the tip 3 is taken out and the direction of puncture by (the moving direction of) the needle 21 are opposite to each other.

Also, the tip 3 is contained in the case 4 in which the puncture mechanism 2 is contained, together with the puncture mechanism 2. This helps ensure that preparation of a member for containing the tip 3 separately from the case 4 can be omitted, and so the body fluid sampling unit 1 is relatively simple in configuration.

FIGS. 7-11 illustrate a second embodiment of the body fluid sampling unit. The following description of the second embodiment primarily discusses aspects or features of this embodiment that differ from the embodiment described above. Features and aspects of the second embodiment that are the same as the earlier embodiment are designated by the same reference numeral and a detailed description of such features is not repeated.

This second embodiment is the same as the first embodiment, except for the configuration of the case. The case 4A of the body fluid sampling unit 1A shown in FIGS. 7-10 includes a first opening 45 formed by opening an upper-side part of a tube wall ranging from the mechanism containing section 42 to the sampling implement containing section 43. The first opening 45 is roughly rectangular in shape when viewed from the upper side.

In addition, the first opening 45 is provided with a plate piece 46 covering the first opening 45. The plate piece 46 is smaller than the first opening 45, when viewed from the upper side. This ensures that a distal end side part (hereinafter referred to as "small opening 451") of the first opening 45 is left open.

Figure 8:
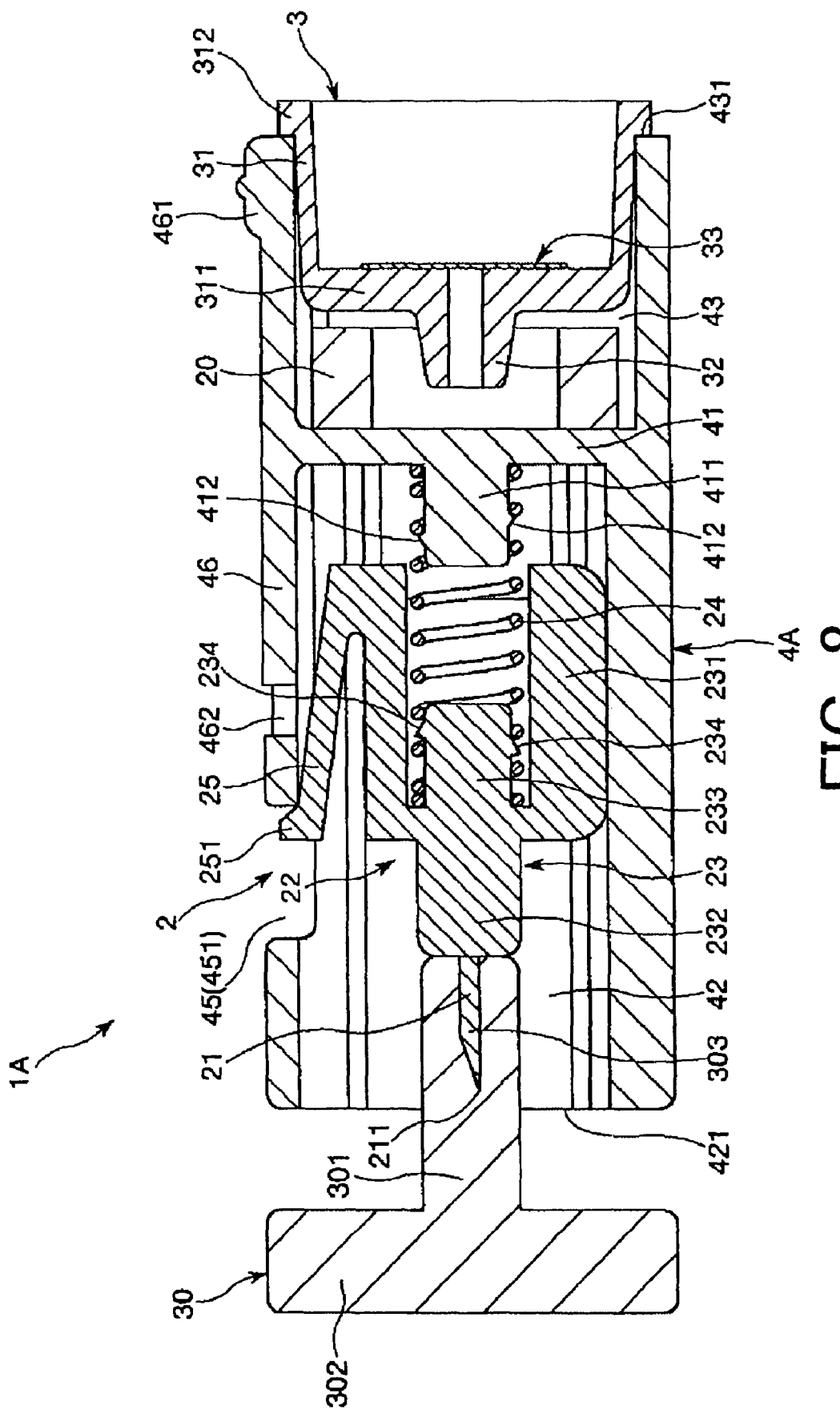
FIG. 8 is a longitudinal cross-sectional view of the body fluid sampling unit shown in FIG. 7 taken along the section line VIII-VIII in FIG. 7.
Figure 9:
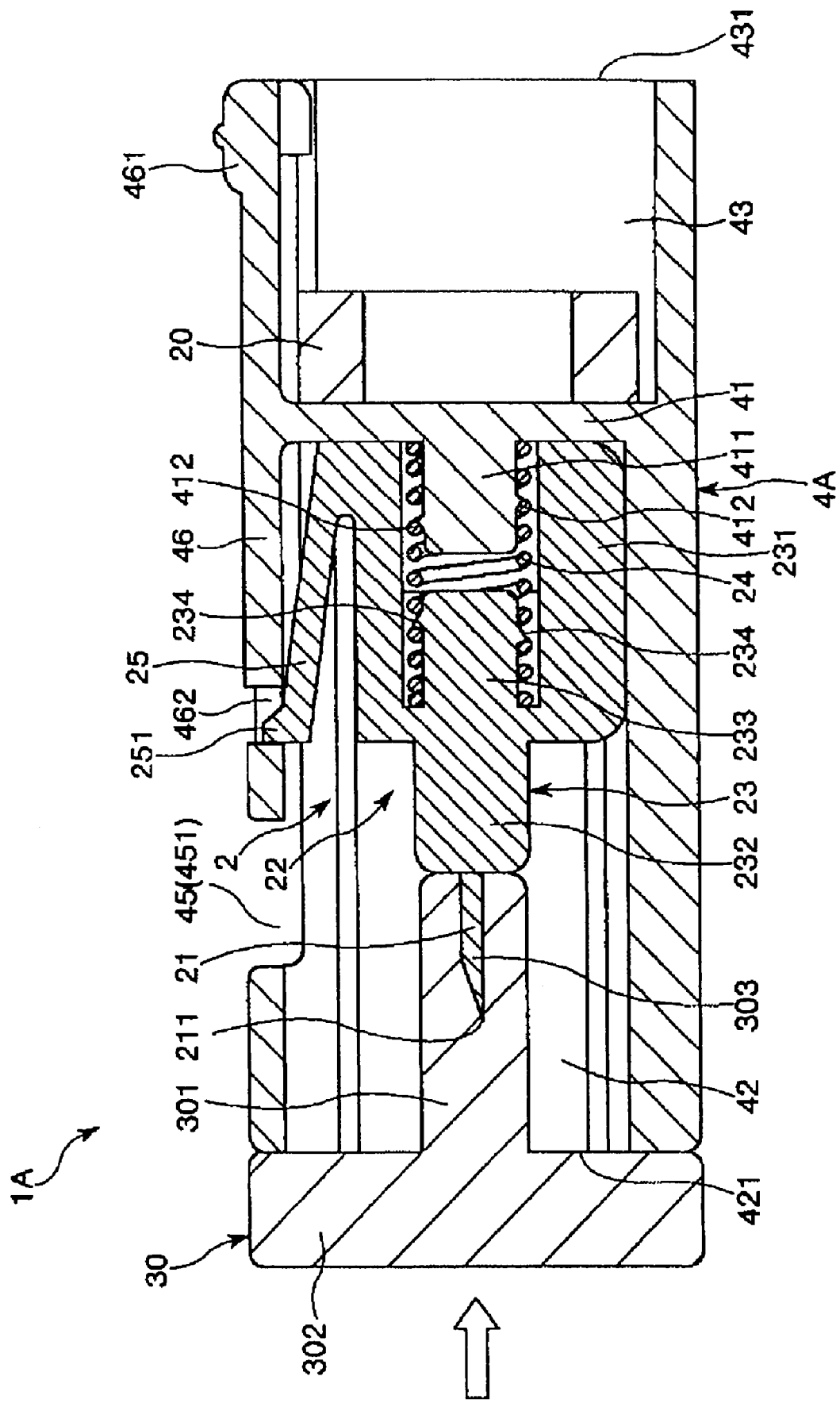
FIG. 9 is a longitudinal cross-sectional view of the body fluid sampling unit of FIG. 7 showing one operating condition of the body fluid sampling unit during use.
Figure 10:
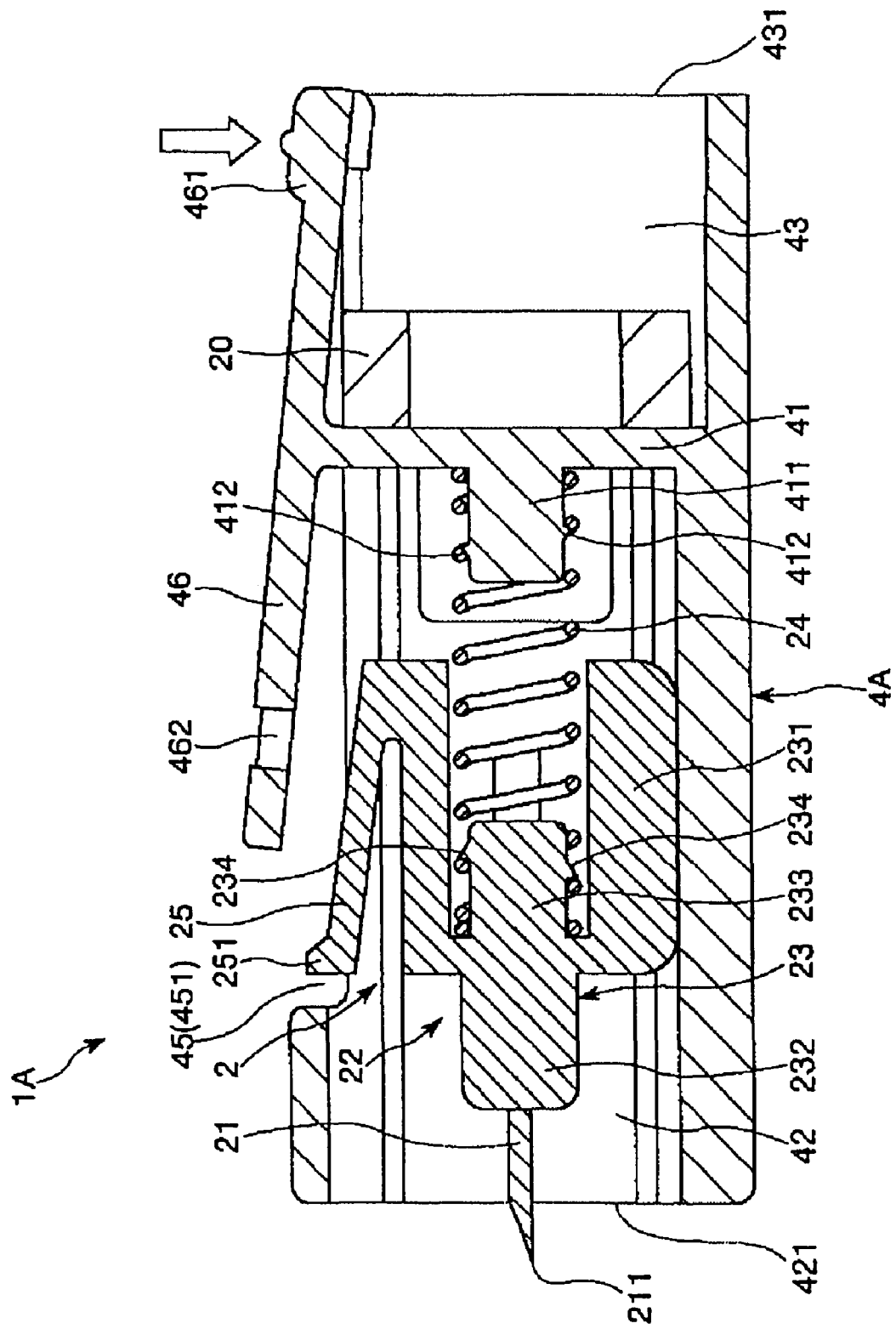
FIG. 10 is a longitudinal cross-sectional view of the body fluid sampling unit showing another operating condition of the second embodiment of the body fluid sampling unit during use.

As shown in FIGS. 8-10, the plate piece 46 is supported by a partition wall 41 at an intermediate part thereof. This ensures that a proximal end part 461 of the plate piece 46 can be depressed downward (see FIG. 10). With the proximal end part 461 of the plate piece 46 depressed downward, a distal end part of the plate piece 46 is displaced upward.

In addition, the plate piece 46 is provided in its distal end part with a second opening 462 penetrating the plate piece 46 in its thickness direction.

In the case 4A configured as above, an engaging piece 25 of the puncture mechanism 2 is engaged with either of the small opening 451 and the second opening 462 according to the operating condition of the puncture mechanism 2.

The operation of the puncture mechanism 2 in the body fluid sampling unit 1A is as follows.

As shown in FIG. 8, when the support section 23 of the puncture mechanism 2 is in its initial position, a coil spring 24 has a natural length. In this instance, the engaging piece 25 has the lock part 251 located at the small opening 451 and in contact with (locked to) the distal end of the plate piece 46. The locating of the support section 23 in a stand-by position is thus maintained, i.e., the support section 23 is inhibited or prevented from unintended movement toward the proximal end side.

With an operating member 30 (support section 23) pushed in the direction of the proximal end starting from the condition shown in FIG. 8, the lock part 251 of the engaging piece 25 moves over the portion between the distal end of the engaging piece 25 and the second opening 462, against an elastic force of the engaging piece 25. Thereafter, the lock part 251 enters into the second opening 462, and is engaged with the second opening 462 as shown in FIG. 9.

The body part 231 of the support section 23 has its proximal end in abutment on the partition wall 41 in the same manner as in the first embodiment. By virtue of this, movement of the support section 23 in the direction of the proximal end is stopped.

In addition, the coil spring 24 is compressed in the same manner as in the first embodiment. As a result, a biasing force is accumulated in the coil spring 24.

With the proximal end part 461 of the plate piece 46 depressed downward starting from the condition shown in FIG. 9, the second opening 462 is raised. This disengages the second opening 462 and the lock part 251 of the engaging piece 25 from each other. The compressed state of the coil spring 24 is thus cleared, and the coil spring 24 expands in the direction of the distal end. As a result, the support section 23 is displaced into a puncture position so that the needle point 211 protrudes from the distal end opening 421. That is, puncture of a fingertip is enabled (see FIG. 10).

Figure 11:
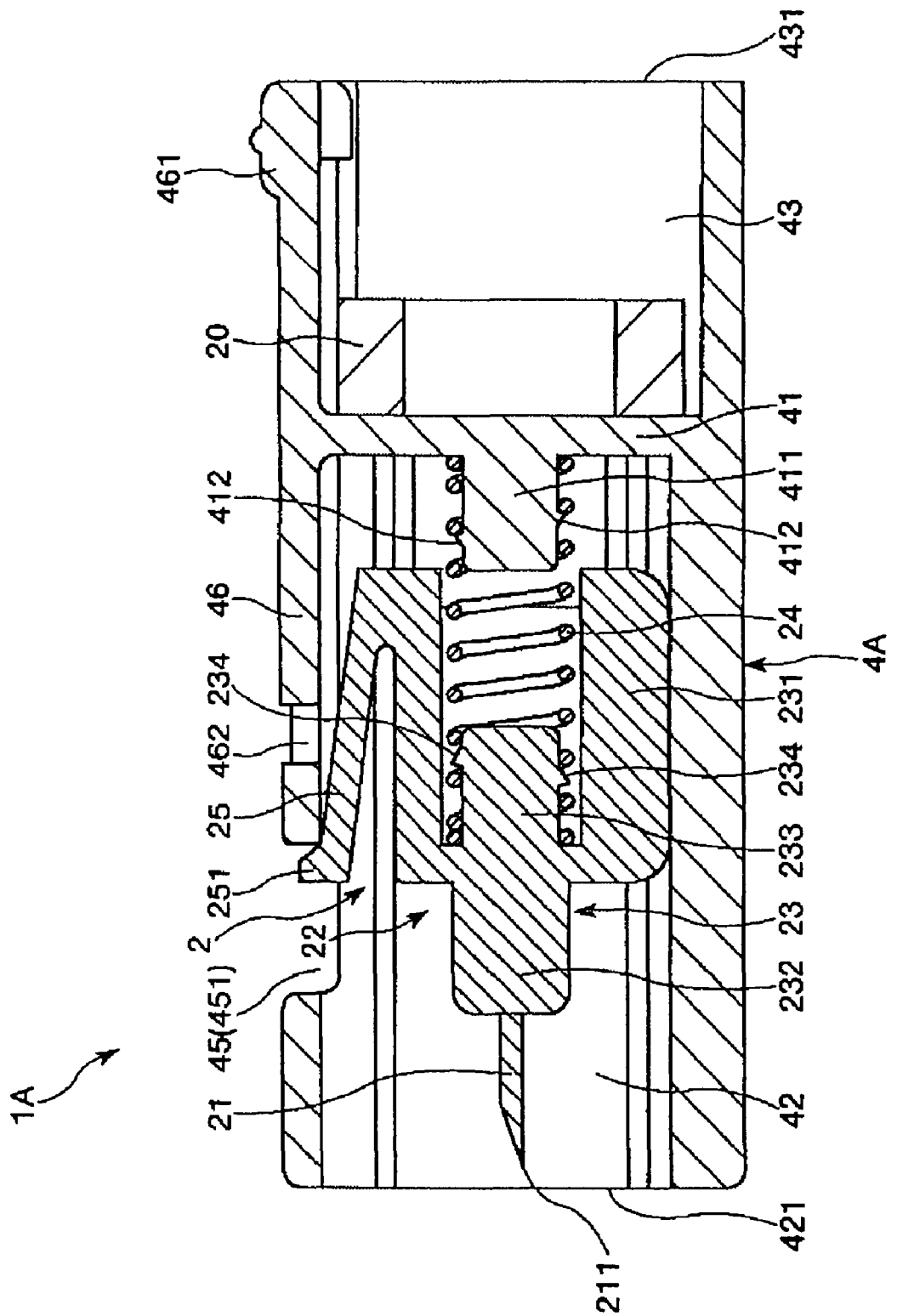
FIG. 11 is a longitudinal cross-sectional view of the body fluid sampling unit showing another operating condition of the second embodiment of the body fluid sampling unit during use.
Figure 12:
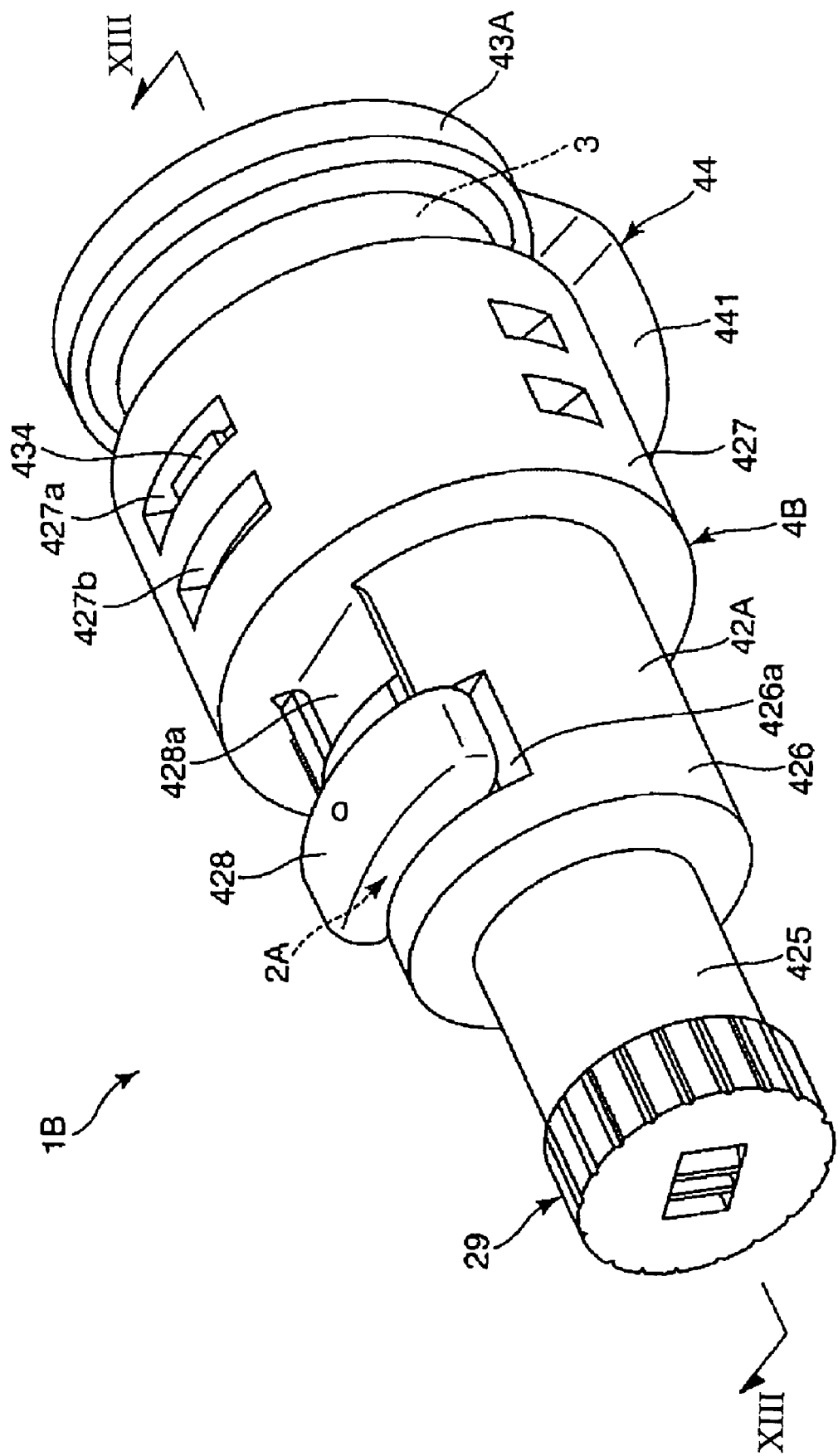
FIG. 12 is a perspective view of a third embodiment of the body fluid sampling unit.

Thereafter, the coil spring 24 returns to the natural length so that the support section 23 is displaced into the initial position as illustrated in FIG. 11.

Thus, in the body fluid sampling unit 1A, a disengaging section (the proximal end part 461 of the plate piece 46) for disengaging the lock part 251 of the engaging piece 25 and the second opening 462 from each other is located at a proximal end part of the body fluid sampling unit 1A. This helps ensure that the proximal end part 461 cannot be depressed downward until the tip 3 is mounted to a component measuring device 100 and released from a sampling implement containing section 43 and that accidental sticking can be advantageously inhibited or prevented from occurring at a unintended timing, such as at the time of mounting the tip 3 or at the time of detaching the operating member 30.

In addition, the body fluid sampling unit 1A may be entirely contained in a packaging material in a gas-tight manner. This makes it possible to maintain a sterile state of the needle 21 and the tip 3 or to maintain a dry state of the tip 3.

FIGS. 12-16 illustrate a third embodiment of the body fluid sampling unit. The following description of the third embodiment primarily discusses aspects or features of this embodiment that differ from the embodiments described above. Features and aspects of the third embodiment that are the same as the earlier embodiments are designated by the same reference numeral and a detailed description of such features is not repeated.

This third embodiment is the same as the first embodiment above, except for the configurations of the case and the puncture mechanism.

The case 4B of a body fluid sampling unit 1B shown in FIGS. 12-16 includes a mechanism containing section 42A composed of an outer tube, and a sampling implement containing section 43A composed of an inner tube slid or positioned inside the mechanism containing section 42A (outer tube) along its longitudinal direction.

The mechanism containing section 42A is composed of a distal end part 425, an intermediate part 426 and a proximal end part 427 which differ in inside diameter. The inside diameter of the distal end part 425 is smaller than the inside diameter of the intermediate part 426. In addition, the inside diameter of the intermediate part 426 is smaller than the inside diameter of the proximal end part 427. Thus, the mechanism containing section 42A increases in inside diameter in a stepwise manner in the direction of the proximal end.

The intermediate part 426 is provided with an opening 426a that opens in (penetrates) an upper-side part of a tube wall of the intermediate part 426. A cantilever-supported pushing piece 428 is formed at the opening 426a. The proximal end of the pushing piece 428 is supported by a boundary part (stepped part) 426b between the intermediate part 426 and the proximal end part 427.

Figure 15:
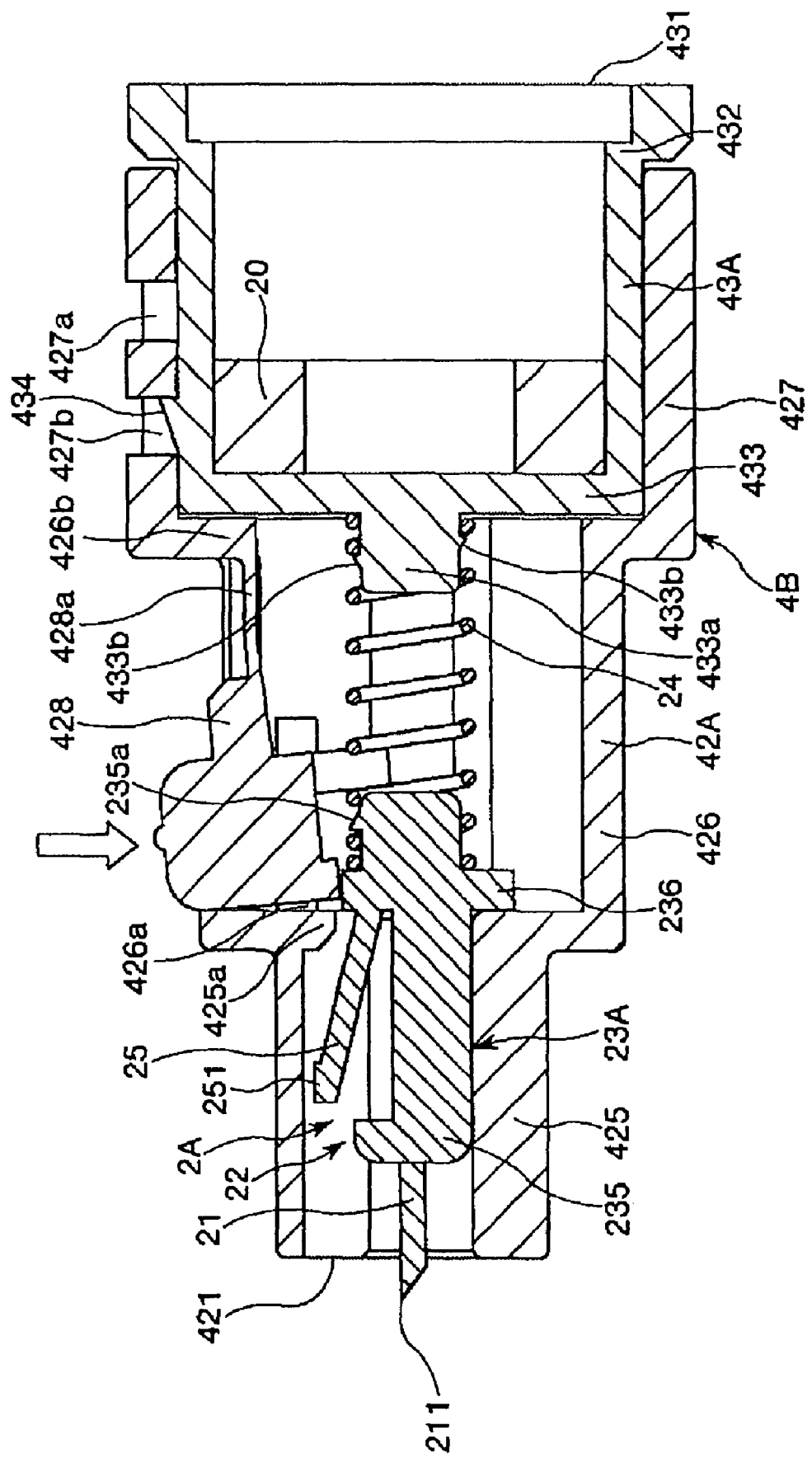
FIG. 15 is a longitudinal cross-sectional view of the body fluid sampling unit showing another operating condition of the third embodiment of the body fluid sampling unit during use.

A portion of the pushing piece 428 in the vicinity of the boundary part 426b is composed of a thin wall part 428a having elasticity. This enables the pushing piece 428 to be easily depressed downward as shown in FIG. 15.

The proximal end part 427 includes a first opening (first engaging part) 427a and a second opening (second engaging part) 427b which both open in (penetrate) the upper-side parts of the tube wall thereof. The second opening 427b is disposed on the distal end side of the first opening 427a. In addition, the first opening 427a and the second opening 427b are each roughly rectangular in shape when viewed from the upper side. A pawl part 434 possessed by a sampling implement containing section 43A is engaged with either of the first opening 427a and the second opening 427b, according to the operating condition of the puncture mechanism 2A.

The sampling implement containing section 43A is movably disposed at the proximal end part 427 of the mechanism containing section 42A. The sampling implement containing section 43A has a wall part 433 at the proximal end thereof, and, as a whole, has a bottomed tube shape.

A projected part 433a is formed at the wall part 433 of the sampling implement containing section 43A and projects in the direction of the distal end. The projected part 433a is cylindrical in outer shape. A proximal end section of a coil spring 24 is fitted over the projected part 433a.

The projected part 433a is provided at its outer peripheral part with a plurality of pawl parts 433b projecting in the outer radial direction. Each of the pawl parts 433b is wedge-shaped so that its height gradually increases in the direction of the proximal end. Each of the pawl parts 433b is in engagement with the proximal end section of the coil spring 24. This prevents the projected part 433a from being slipped from the proximal end section of the coil spring 24, i.e., this makes it possible to support and fix the proximal end section of the coil spring 24.

In addition, the sampling implement containing section 43A is provided with a pawl part 434 at an outer peripheral part thereof. The pawl part 434 is wedge-shaped so that its height gradually increases in the direction of the proximal end. As has been above-mentioned, the pawl part 434 is engaged with either of the first opening 427a and the second opening 427b.

A support section 23A of the puncture mechanism 2A in this embodiment includes a cylindrically shaped body part 235 and a contact part 236 formed as a projection at the outer peripheral part of the body part 235.

A proximal end part of the body part 235 is provided at its outer peripheral part with a pawl part 235a projecting in the radial direction. The pawl part 235a is wedge-shaped so that its height gradually increases in the direction of the distal end. The pawl part 235a is in engagement with a distal end section of the coil spring 24. This prevents the proximal end part of the body part 235 from being drawn off from the distal end section of the coil spring 24, i.e., this makes it possible to support and fix the distal end section of the coil spring 24.

An engaging piece 25 is cantilever-supported at an intermediate part of the body part 235.

The contact part 236 is provided at a lower part of the body part 235, in the state of projecting downward. The contact part 236 is a portion which is block-like in shape.

In addition, a needle 21 is fitted (covered) with a cap 29 configured in substantially the same manner as the operating member 30 mentioned above. The cap 29 is detached from the needle 21 at the time of performing a puncturing operation.

Figure 13:
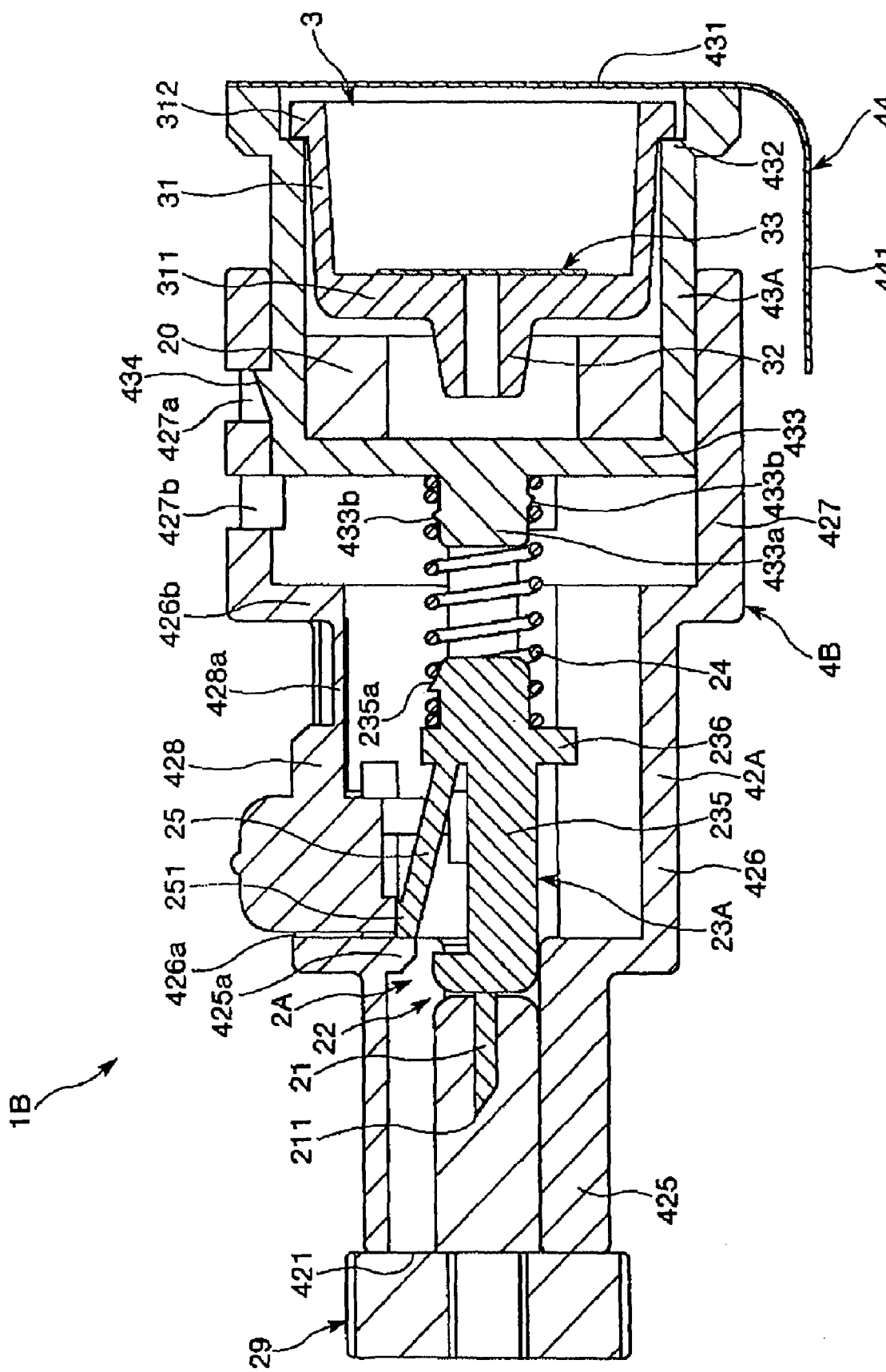
FIG. 13 is a longitudinal cross-sectional view of the body fluid sampling unit shown in FIG. 12 taken along the section line XIII-XIII in FIG. 12.

The operation of the body fluid sampling unit 1B configured as above is as follows. As shown in FIG. 13 (and in FIG. 12 also), when the body fluid sampling unit 1B is in an unused state, the sampling implement containing section 43A has its pawl part 434 in engagement with the first opening 427a of the mechanism containing section 42A.

In this situation, the support section 23A in the puncture mechanism 2A is in its initial position; namely, the coil spring 24 is in the state having its natural length. In addition, the engaging piece 25 has its lock part 251 in engagement with (in abutment on) a boundary part (stepped part) 425a between the distal end part 425 and an intermediate part 426 of the case 4B.

This prevents the needle 21 (support section 23A) from unintended movement so that accidental sticking by a needle point 211 due to movement of the needle 21 can be relatively reliably prevented.

When a tip mounting section 103 of a component measuring device 100 is pushed from the proximal end side into the tip 3 in the condition shown in FIG. 13, the sampling implement containing section 43A moves (slides) in the direction of the distal end relative to the mechanism containing section 42A, together with the tip 3. As a result, the pawl part 434 of the sampling implement containing section 43A is disengaged from the first opening 427a in the mechanism containing section 42A, and the pawl part 434 becomes engaged with the second opening 427b of the mechanism containing section 42A. In addition, due to the engagement of the pawl part 434 with the second opening 427b, movement of the sampling implement containing section 43A relative to the mechanism containing section 42A is stopped, i.e., the position of the sampling implement containing section 43A relative to the mechanism containing section 42A is fixed.

In addition, in the puncture mechanism 2A, the mechanism containing section 42A is brought closer to the support section 23A so that the coil spring 24 is compressed between the mechanism containing section 42A and the support section 23A. As a result, a biasing force is accumulated in the coil spring 24.

Figure 14:
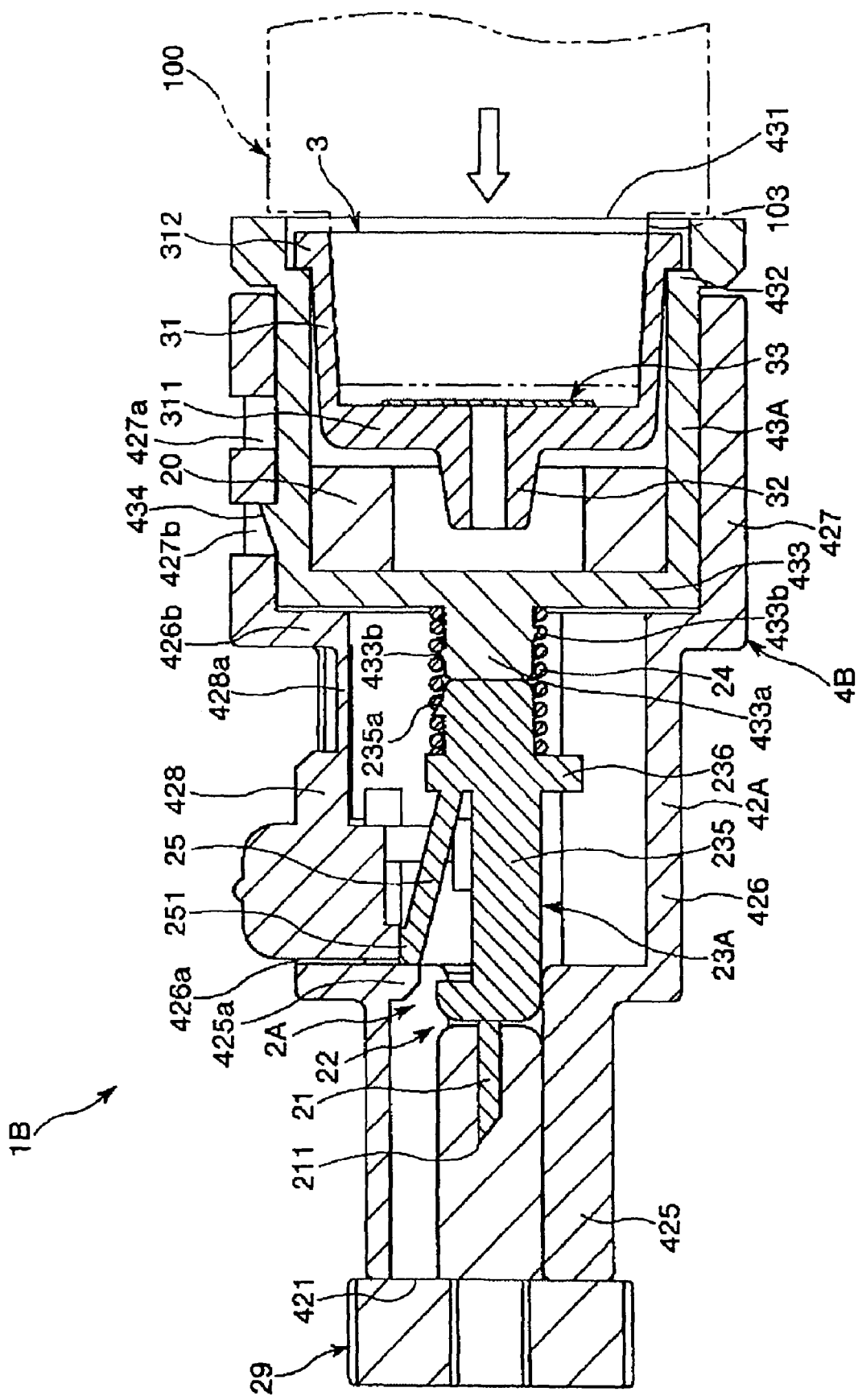
FIG. 14 is a longitudinal cross-sectional view of the body fluid sampling unit of FIG. 12 showing an operating condition of the body fluid sampling unit during use.

By such an operation starting from the initial position, the support section 23A is displaced into a stand-by position, i.e., the puncture mechanism 2A (body fluid sampling unit 1B) is put into the condition shown in FIG. 14.

With the pushing piece 428 depressed downward starting from the condition shown in FIG. 14, the lock part 251 of the engaging piece 25 and the boundary part 425a are disengaged from each other. In this instance, the compressed state of the coil spring 24 is cleared, and the coil spring 24 expands in the direction of the distal end. This displaces the support section 23A into a puncture position so that the needle point 211 protrudes from a distal end opening 421 as shown in FIG. 15, i.e., puncture of a fingertip is enabled.

When the support section 23A is located in the puncture position, a contact part 236 of the support section 23A abuts on the boundary part 425a. This prevents the needle point 211 from excessively protruding through the distal end opening 421.

Figure 16:
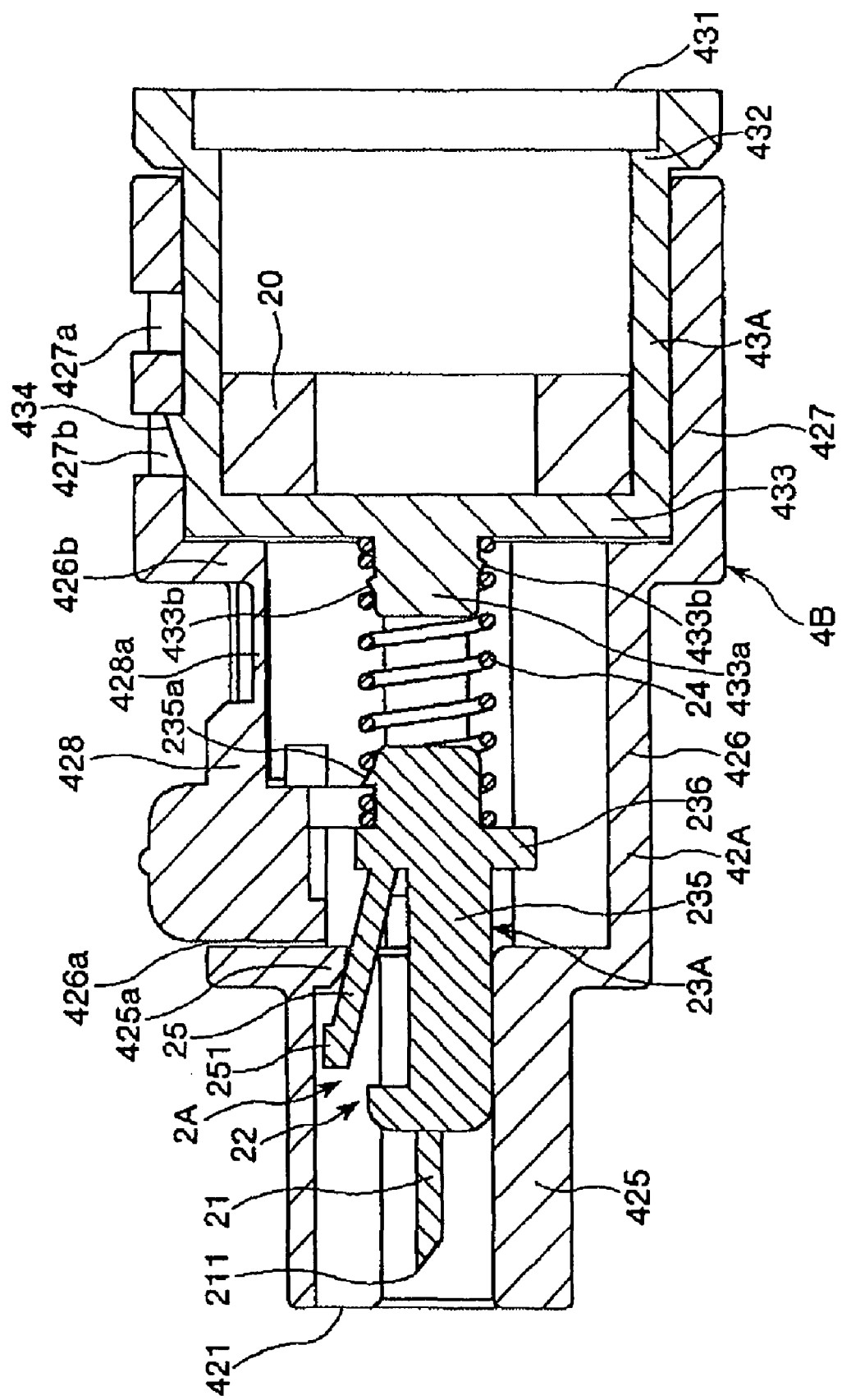
FIG. 16 is a longitudinal cross-sectional view of the body fluid sampling unit showing another operating condition of the third embodiment of the body fluid sampling unit during use.
Figure 17:
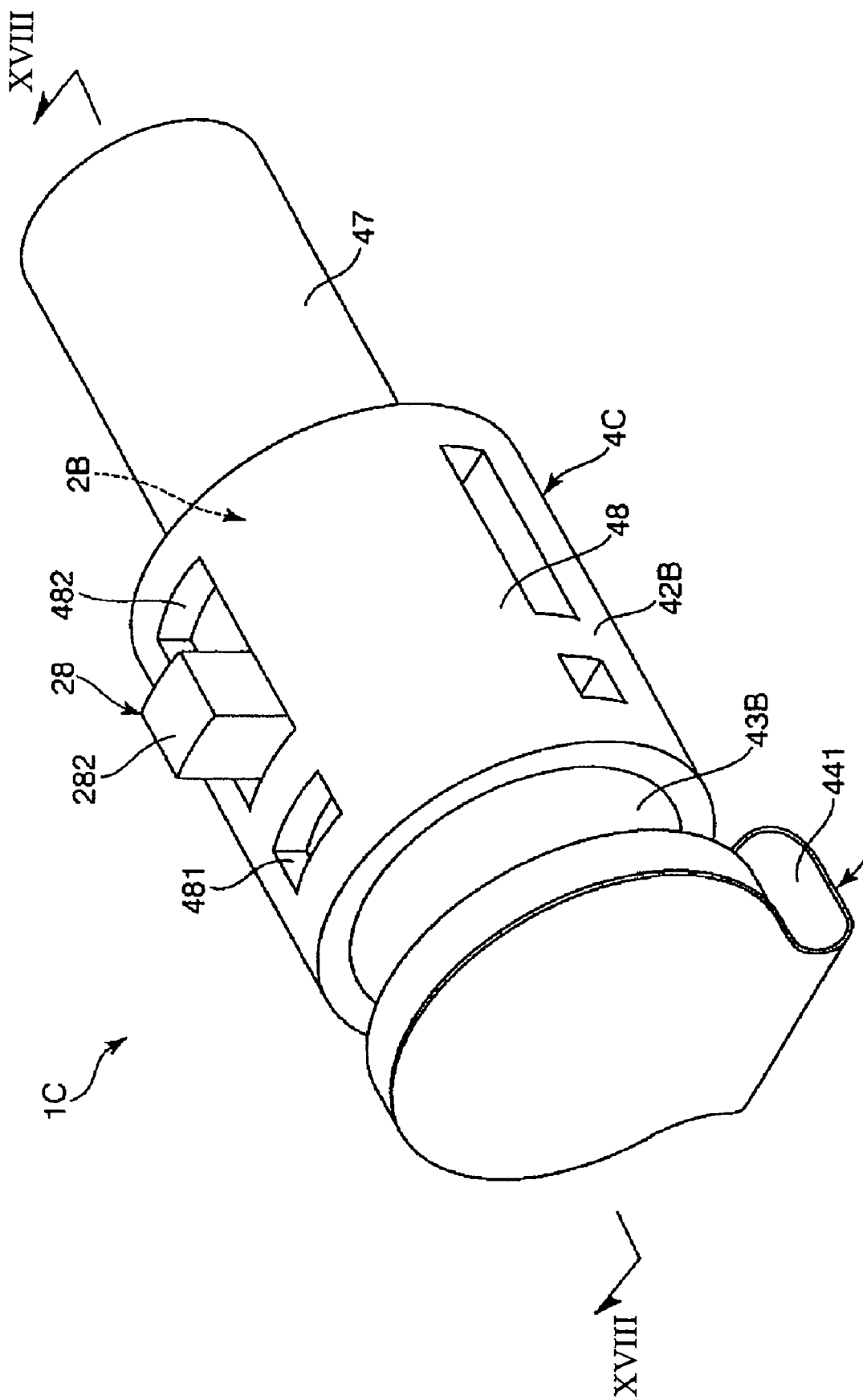
FIG. 17 is a perspective view of a fourth embodiment of the body fluid sampling unit.

Thereafter, the coil spring 24 returns to the condition of its natural length so that the support section 23A is displaced into its initial position (as depicted in FIG. 16.

After the position of the sampling implement containing section 43A relative to the mechanism containing section 42A is fixed, the tip 3 naturally is spaced away from the sampling implement containing section 43A, together with a component measuring device 100.

Thus, in the body fluid sampling unit 1B, the puncture mechanism 2A (support section 23A) is displaced into a stand-by position (this operation will hereinafter be referred to as "charging operation") simultaneously (inclusive of substantially simultaneously) with the mounting operation of mounting the tip 3 to the component measuring device 100. In other words, in the body fluid sampling unit 1B, the mounting operation is utilized also as the charging operation.

This makes it unnecessary to perform the charging operation separately from the mounting operation as in the first embodiment. Therefore, operational aspects of the body fluid sampling unit 1B in sampling blood is further enhanced.

FIGS. 17-21 illustrate a fourth embodiment of the body fluid sampling unit. The following description of the fourth embodiment primarily discusses aspects or features of this embodiment that differ from the embodiments described above. Features and aspects of the fourth embodiment that are the same as the earlier embodiments are designated by the same reference numeral and a detailed description of such features is not repeated.

This fourth embodiment is the same as the third embodiment above, except for the configurations of the case and the puncture mechanism. The case 4C of the body fluid sampling unit 1C shown in FIGS. 17-21 includes a mechanism containing section 42B composed of an outer tube, and a sampling implement containing section 43B composed of an inner tube slid or positioned inside the mechanism containing section 42B (outer tube) along its longitudinal direction.

The mechanism containing section 42B is changed (enlarged) in inside diameter at an intermediate part thereof, and is divided at the part of the change (boundary part or stepped part 429) into a small diameter part (reduced diameter part) 47 and an enlarged diameter part 48 whose inside diameter is enlarged as compared with the small diameter part 47.

The small diameter part 47 has a wall part 471 at the proximal end thereof and, as a whole, has a bottomed tube shape.

The enlarged diameter part 48 has a first opening (first engaging part) 481 and a second opening (second engaging part) 482 which open in (penetrate) upper-side parts of the tube wall thereof. The second opening 482 is disposed on the proximal end side of the first opening 481.

The first opening 481 and the second opening 482 are roughly rectangular in shape as viewed from the upper side. In addition, the second opening 482 is larger (longer) than the first opening 481 in size in the longitudinal direction of the enlarged diameter part 48.

A pawl part 434 possessed by a sampling implement containing section 43B is engaged with either of the first opening 481 or the second opening 482 according to the operating condition of a puncture mechanism 2B.

The sampling implement containing section 43B having a bottomed tube shape is movably disposed in the enlarged diameter part 48 of the mechanism containing section 42B.

The sampling implement containing section 43B has a guide part 436 provided on the proximal end side of a wall part 433, with a clearance 435 between the guide part 436 and the wall part 433. The guide part 436 is plate-shaped (inclusive of plate-like shaped), and is disposed parallel (inclusive of substantially parallel) to the wall part 433.

In addition, the wall part 433 and the guide part 436 are provided respectively with through-holes 433c, 436a that pierce or penetrate the wall part 433 and the guide part 436 respectively. The through-holes 433c, 436a are disposed coaxially with each other. The through-hole 436a is larger than the through-hole 433c.

The puncture mechanism 2B contained in the mechanism containing section 42B includes a support section 23B, a first coil spring 26, a second coil spring 27, and an operating member (pushing member) 28.

Figure 18:
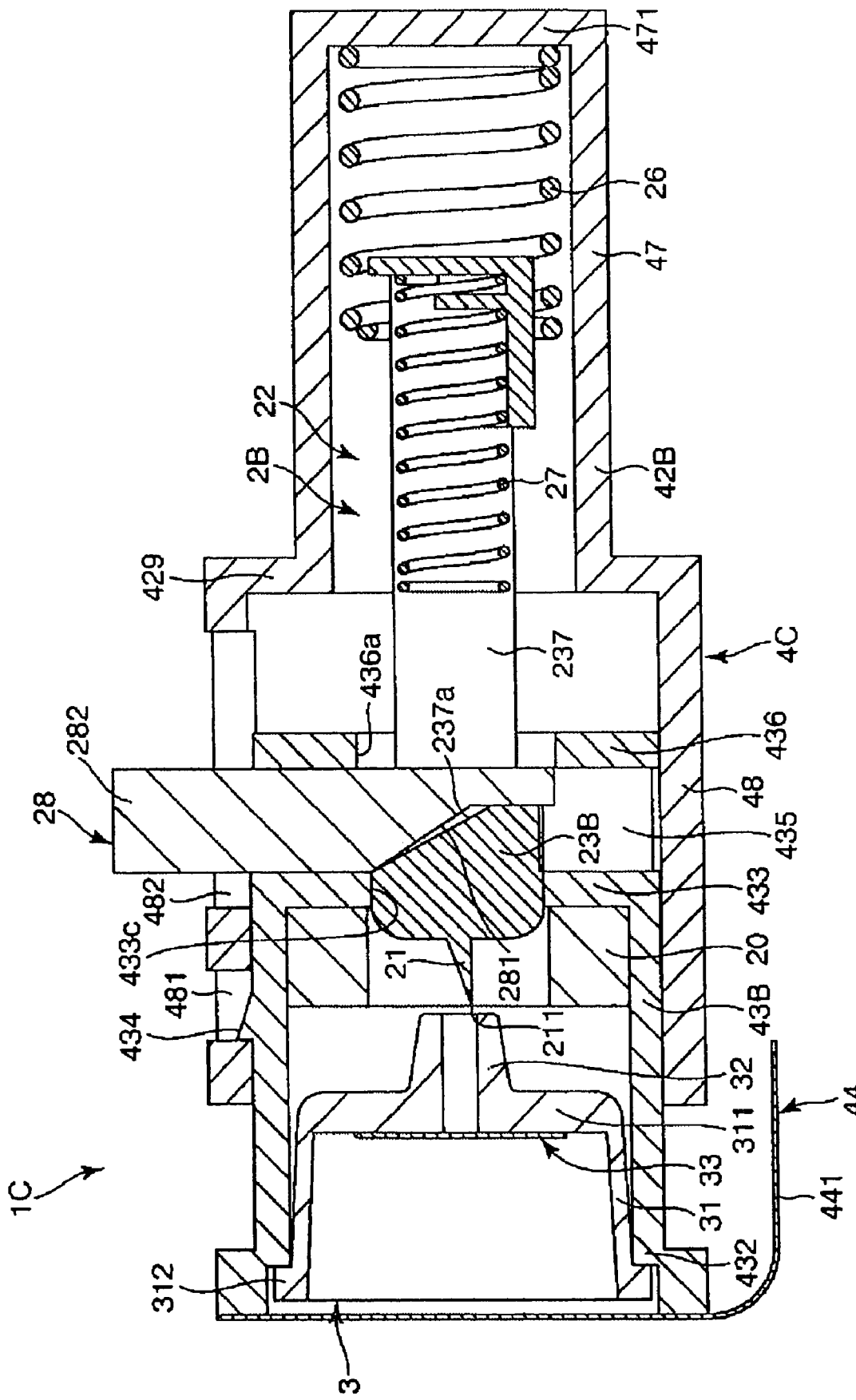
FIG. 18 is a longitudinal cross-sectional view of the body fluid sampling unit shown in FIG. 17 taken along the section line XVIII-XVIII in FIG. 17.
Figure 19:
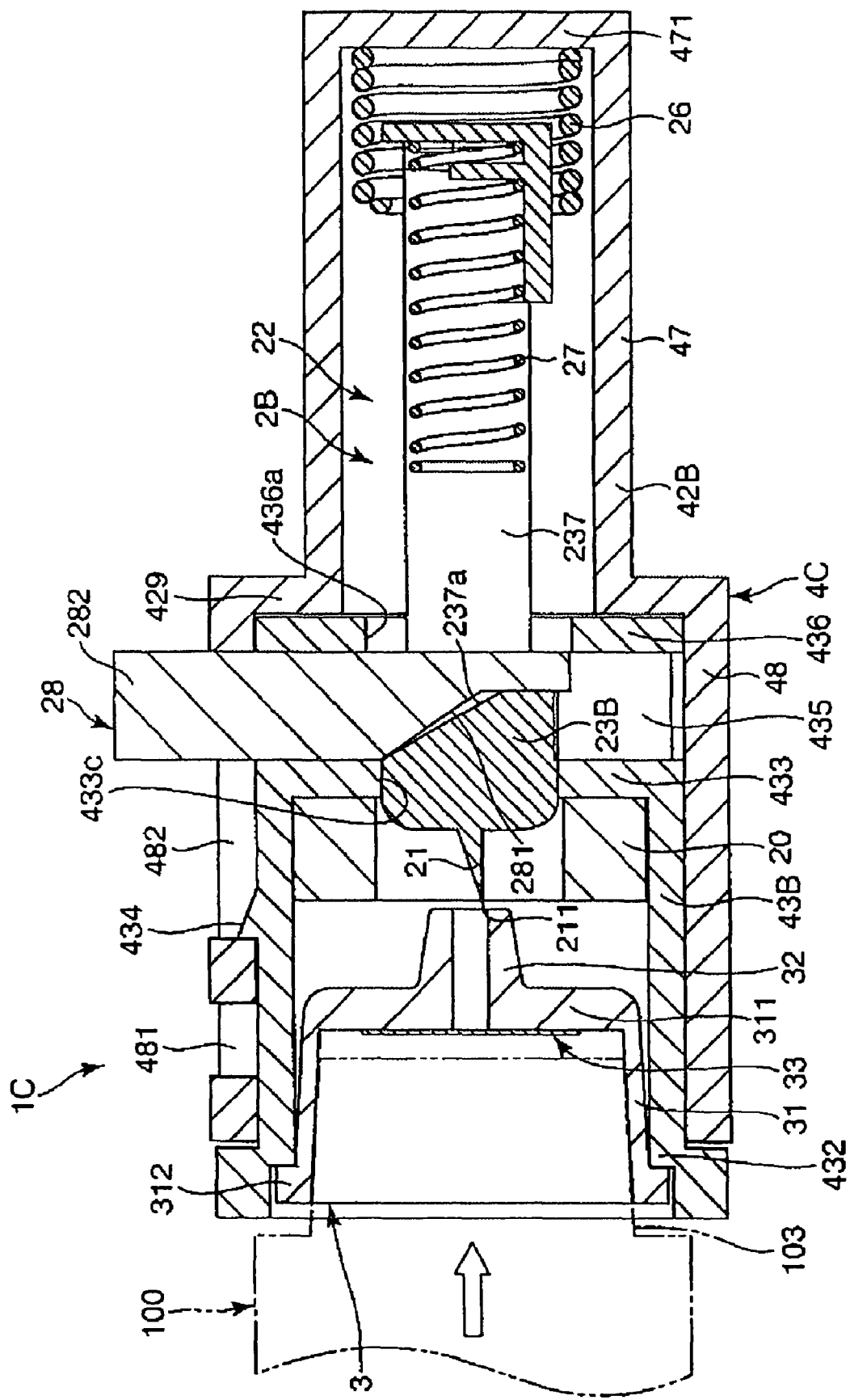
FIG. 19 is a longitudinal cross-sectional view of the body fluid sampling unit of FIG. 17 showing an operating condition of the body fluid sampling unit during use.
Figure 20:
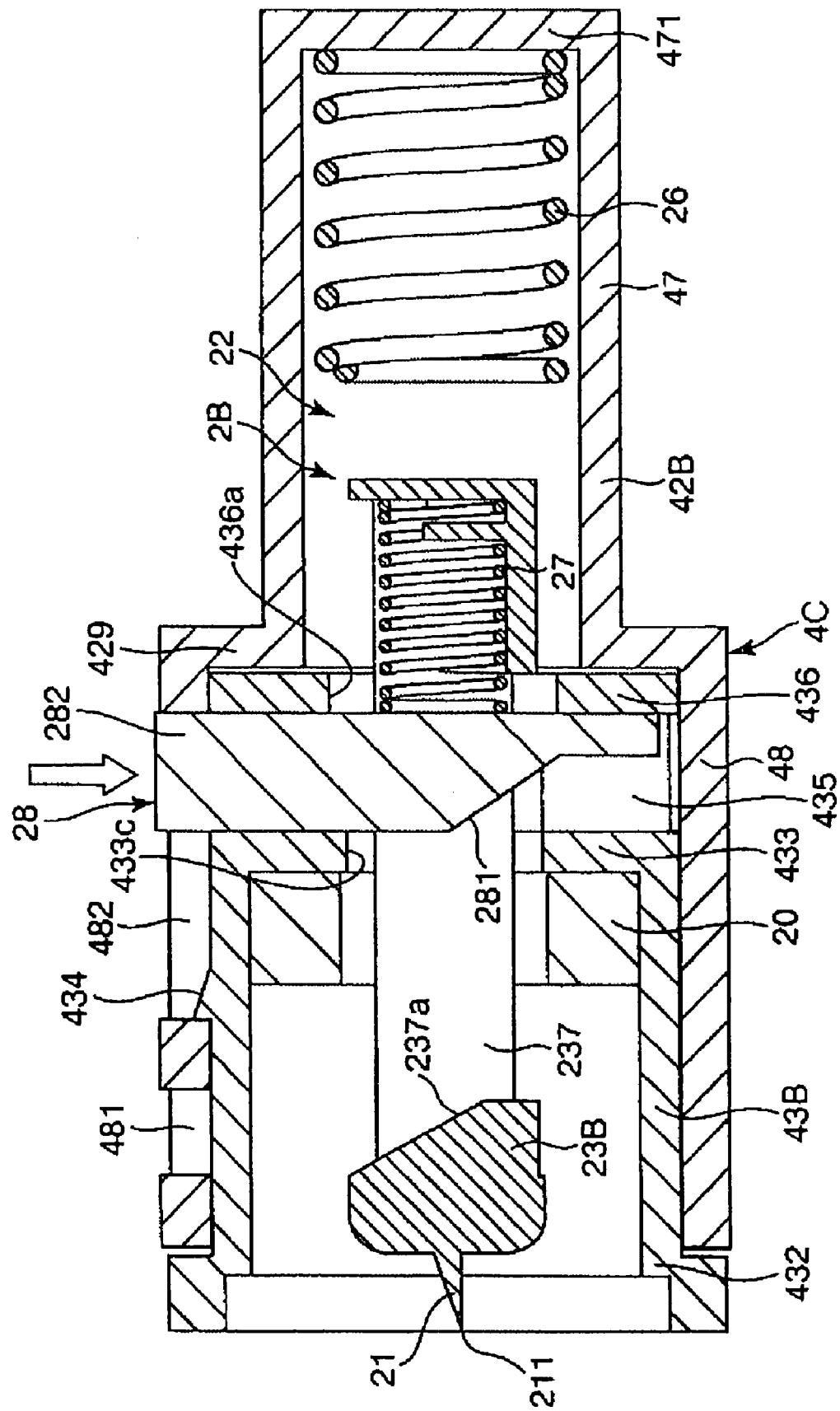
FIG. 20 is a longitudinal cross-sectional view of the body fluid sampling unit showing another operating condition of the fourth embodiment of the body fluid sampling unit during use.

The support section 23B is cylindrical in outer shape. When the body fluid sampling unit 1C is in an unused state, a distal end part of the support section 23B is fitted (is in frictional engagement with) the through-hole 433c in the wall part 433 of the sampling implement containing section 43B as seen in FIGS. 18 and 19.

In addition, the support section 23B has a hollow part 237 opening in the vertical directions. The hollow part 237 is provided at its distal end part with an inclined surface 237a inclined relative to the longitudinal direction of the hollow part 237. The second coil spring 27 and the operating member 28 are disposed in the hollow part 237.

A proximal end part of the second coil spring 27 is supported on and is fixed to a proximal end part of the hollow part 237 (support section 23B). The distal end of the second coil spring 27 is a free end (i.e., not in engagement with another part) when the body fluid sampling unit 1C is in the unused state.

The operating member 28 is disposed to be vertically movable inside the clearance 435 in the sampling implement containing section 43B along the guide part 436 (wall part 433). In addition, the operating member 28 penetrates the hollow part 237 in the support section 23B.

The operating member 28 possesses a quadrangular prism shape. The operating member 28 is provided at a lower part thereof with an inclined surface 281 opposed to the inclined surface 237a of the support section 23B. In addition, an upper part 282 of the operating member 28 protrudes through the second opening 482.

The first coil spring 26 has its proximal end supported on and fixed to the wall part 471 of the small diameter part 47. The distal end of the first coil spring 26 is in abutment on a projection (not shown) provided at a proximal end part of the support section 23B when the body fluid sampling unit 1C is in the unused state.

The operation of the body fluid sampling unit 1C configured as above is as follows.

As shown in FIG. 18 (and in FIG. 17 also), when the body fluid sampling unit 1C is in the unused state, the pawl part 434 of the sampling implement containing section 43B is in engagement with the first opening 481 of the mechanism containing section 42B.

In this instance, in the puncture mechanism 2B, the support section 23B is in its initial position, i.e., the first coil spring 26 and the second coil spring 27 are in the condition having their natural lengths. In addition, a distal end part of the support section 23B is fitted in the through-hole 433c of the sampling implement containing section 43B, and the inclined surface 281 of the operating member 28 is in contact with the inclined surface 237a of the support section 23B.

When a tip mounting section 103 of a component measuring device 100 is pushed from the distal end side into the tip 3 in the condition shown in FIG. 18, the sampling implement containing section 43B is moved (slid) in the direction of the proximal end relative to the mechanism containing section 42B, together with the tip 3. This disengages the pawl part 434 of the sampling implement containing section 43B from the first opening 481 of the mechanism containing section 42B, and the pawl part 434 is engaged with the second opening 482 of the mechanism containing section 42B. In addition, due to the engagement of the pawl part 434 with the second opening 482, the position of the sampling implement containing section 43B relative to the mechanism containing section 42B is fixed.

In the puncture mechanism 2B, the support section 23B is moved in the direction of the proximal end, together with the sampling implement containing section 43B. This brings the support section 23B and the wall part 471 of the mechanism containing section 42B closer to each other, so that the first coil spring 26 is compressed between them. As a result, a biasing force is accumulated in the first coil spring 26.

In addition, the operating member 28 also is moved in the direction of the proximal end, together with the sampling implement containing section 43B (support section 23B). By this movement, the upper part 282 of the operating member 28 is moved inside the second opening 482 in its longitudinal direction.

By such an operation from the initial position, the support section 23B is displaced into a stand-by position, i.e., the puncture mechanism 2B (body fluid sampling unit 1C) is put into the condition shown in FIG. 19.

With the operating member 28 depressed downward starting from the condition shown in FIG. 19, the inclined surface 281 of the operating member 28 pushes the inclined surface 237a of the support section 23B in the direction of the distal end. By virtue of this, the frictional engagement between the support section 23B and the through-hole 433c of the sampling implement containing section 43B is released. In this instance, the compressed state of the first coil spring 26 is cleared, and the first coil spring 26 expands in the direction of the distal end. As a result, the support section 23B is displaced into a puncture position, and puncture of a fingertip is enabled (see FIG. 20).

Figure 21:
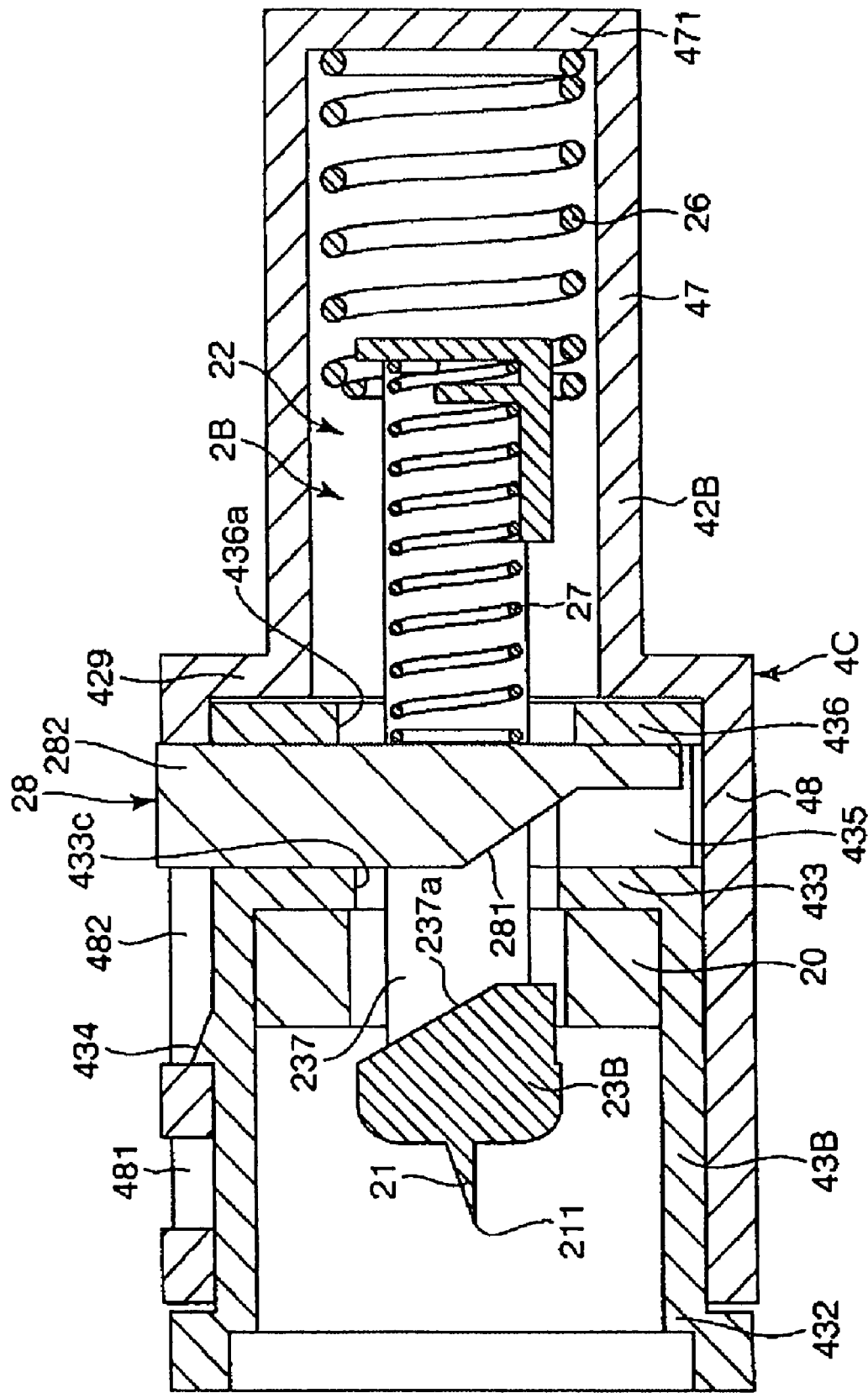
FIG. 21 is a longitudinal cross-sectional view of the body fluid sampling unit showing another operating condition of the fourth embodiment of the body fluid sampling unit during use.

In addition, associated with the displacement of the support section 23B to the puncture position, the second coil spring 27 is also moved in the direction of the distal end. As the second coil spring 27 thus moves, the distal end abuts on the operating member 28, whereby the second coil spring 27 is further compressed between the operating member 28 and a proximal end part of the hollow part 237. The second coil spring 27 thus compressed in this way tends to return to its natural length. This displaces the support section 23B from the puncture position to the initial position as seen in FIG. 21.

Thus, in the body fluid sampling unit 1C, the charging operation can be performed simultaneously (inclusive of substantially simultaneously) with the mounting operation of mounting the tip 3 to a component measuring device 100. This makes it unnecessary to perform the charging operation separately from the mounting operation as in the first embodiment. Therefore, operational aspects of the body fluid sampling unit 1C in sampling blood is enhanced. In addition, cleanliness of a needle point 211 is maintained to an extent comparable to the cleanliness of the tip 3 so that a needle point protective member can be omitted if desired, and an operation of removing such a protective member can be advantageously omitted.

This illustrated embodiment of the body fluid sampling unit 1C has two coil springs, i.e., the first coil spring 26 for displacing the support section 23B to the puncture position (protruding a needle 21) and the second coil spring 27 for returning the support section 23B to the initial position. However, this embodiment is not limited in this regard. For example, a configuration may be adopted in which the support section 23B is displaced to each position by a single coil spring.

Figure 22:
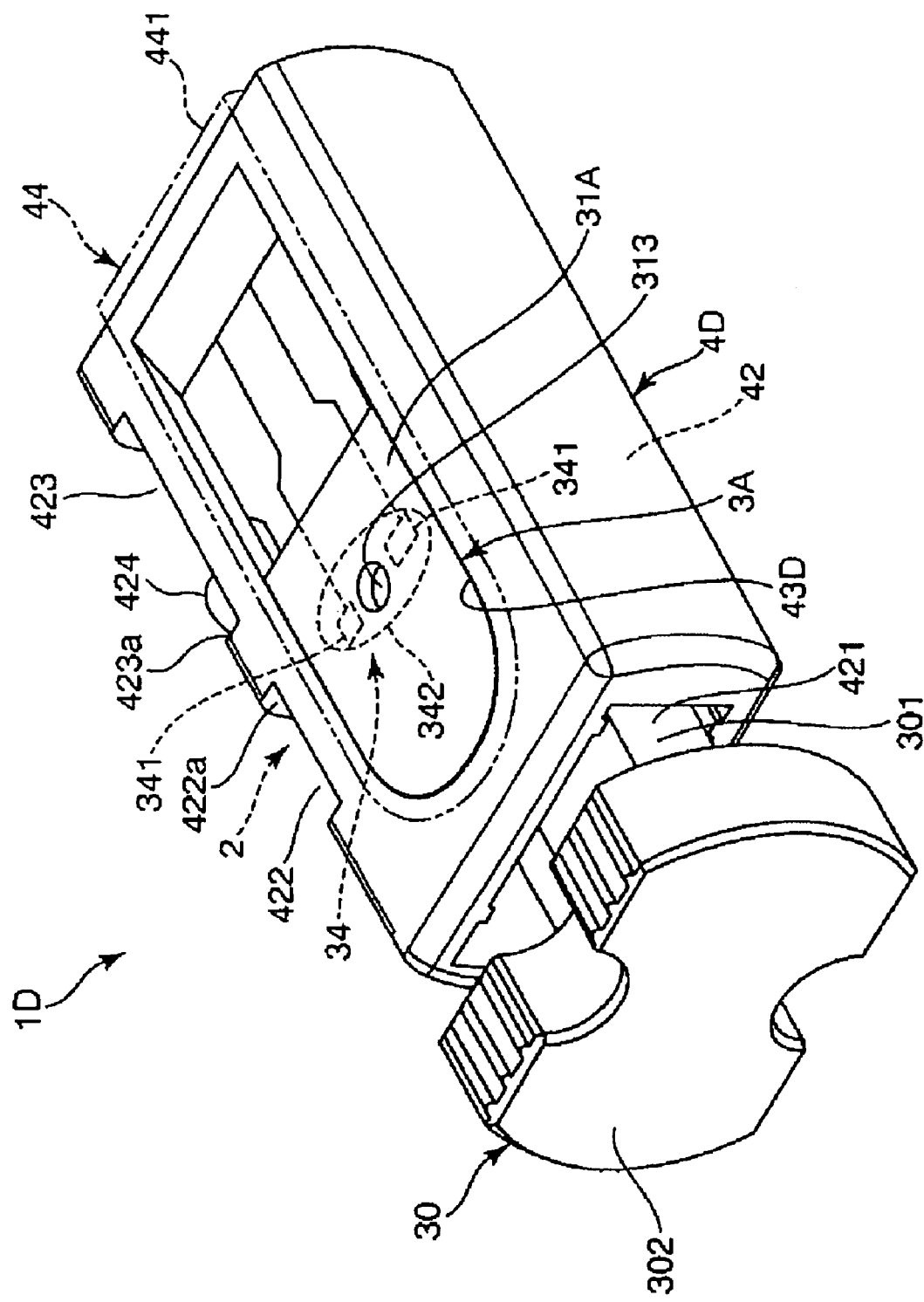
FIG. 22 is a perspective view showing a fifth embodiment of the body fluid sampling unit.

FIG. 22 is a perspective view showing a fifth embodiment of the body fluid sampling unit according to the present invention. The following description of the fifth embodiment primarily discusses aspects or features of this embodiment that differ from the embodiments described above. Features and aspects of the fifth embodiment that are the same as the earlier embodiments are designated by the same reference numeral and a detailed description of such features is not repeated.

This embodiment is the same as the first embodiment above, except for the configuration of the tip. The case 4D of the body fluid sampling unit ID shown in FIG. 22 includes the sampling implement containing section 43D which is provided or located at an outer peripheral section (side section) of the case 4D. The sampling implement containing section 43D has a concave portion obtained by concaving an outer peripheral section of the case 4D.

A tip 3A is contained in the sampling implement containing section 43. The tip 3A includes a tip body 31A having a hollow plate-like shape, and a sensor section 34 contained (disposed) in the tip body 31A as a detecting section for detecting the quantity of glucose in blood.

A surface on one side of the tip body 31A is provided with an opening 313 communicating with the inside of the tip body 31A. The opening 313 is a portion which functions as an introducing section for introducing blood into the sensor section 34.

The sensor section 34 includes a pair of electrodes 341, and a reagent coated part or reagent carrying part 342 coated with a reagent.

The two electrodes 341 are provided, with a spacing therebetween, by coating or printing in the tip body 31A. The electrodes 341 are electrically connected to a component measuring device 100 (not shown) in the condition where the tip 3A is mounted to the component measuring device 100.

The reagent coated part 342 is so provided as to make contact with the two electrodes 341 and include an area of the electrodes 341. In the condition where the tip 3A is mounted to the component measuring device, the reagent coated part 342 (reagent) reacts with glucose in the blood flowed in through the opening 313, generating a current between the two electrodes 341. The quantity of glucose in the blood can be detected according to the current.

The reagent contained in the reagent coated part 342 is not particularly limited. For example, an appropriate combination of a glucose oxidase, which is an oxidoreductase, with an electron acceptor such as potassium ferricyanide and ferrocene derivatives is used. Incidentally, while the two electrodes 341 function as a working electrode and a counter electrode, a three-electrode system may be adopted which includes a third electrode as a reference electrode in addition to the two electrodes.

The body fluid sampling unit described above is intended to be discarded after mounting the body fluid sampling implement to the component measuring device, performing puncture of a living body surface and measuring a predetermined component in the body fluid let flow out. Namely, the body fluid sampling unit is discarded after being used one time. In view of this, the body fluid sampling unit inclusive of the puncture mechanism is configured to be simple in structure.

While the embodiments of the body fluid sampling unit shown in the drawings have been described above, the invention is not limited to these specific embodiments. The component parts of the body fluid sampling unit can be replaced by those of arbitrary configurations which function in a manner that is the same, similar or equivalent to the functional attributes of the component parts in the embodiments described above. Additional components or structures may be added to the different embodiments.

In addition, the body fluid sampling unit may be a combination of two or more configurations (features) of the above embodiments.

For example, the detecting section in the second to fourth embodiments is not limited to the one composed of the test paper but may be composed of a sensor section in the same manner as in the fifth embodiment.

Also, each of the body fluid sampling units in the first embodiment and the third to fifth embodiments may be contained in a packaging material, in the same manner as in the body fluid sampling unit in the second embodiment.

The principles, embodiments and modes of operation have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A body fluid sampling unit comprising:
a container having an interior;
a needle positioned in the interior of the container, the needle possessing a sharp needle point at a distal end of the needle;
at least one spring positioned in the interior of the container;
the at least one spring being operatively engageable with the needle and being configured to accumulate a spring bias to be applied to the needle to move the needle in a puncturing direction to puncture a living body surface with the needle point;
a body fluid sampling implement removably positioned in the interior of the container:
the body fluid sampling implement comprising: an introducing section for conveying body fluid flowing out from a puncture portion of the living body surface punctured with the needle point; a reagent containing part positioned adjacent the introducing section to receive the body fluid conveyed by the introducing section, the reagent containing part comprising a reagent adapted to interact with a predetermined component in the body fluid; and a mounted section configured to be mounted to a component measuring device for measuring a quantity and/or property of the predetermined component; and
wherein the container comprises an inner tube movably positioned within an outer tube, the body fluid sampling implement being positioned inside the inner tube, the outer tube comprising first and second openings, the inner tube comprising a pawl engaging the first opening, the body fluid sampling implement being configured to be mounted to the component measuring device while the body fluid sampling implement is contained in the sampling implement containing section by pushing the component measuring device towards the body fluid sampling implement to engage the body fluid sampling implement with the component measuring device, said pushing causing the inner tube to move within the outer tube to cause the pawl to be released from the first opening and to engage the second opening.

2. The body fluid sampling unit as set forth in claim 1, wherein the interior of the container comprises a sampling implement containing section in which is positioned the body fluid sampling implement, the sampling implement containing section being covered by a removable membrane member which seals the sampling implement containing section in an air-tight manner.

3. A body fluid sampling unit comprising:
a puncture mechanism comprising a needle possessing a sharp needle point at a distal end of the needle, and drive means for operating the needle to puncture a living body surface with the needle point;
a body fluid sampling implement comprising an introducing section for introducing a body fluid flowing out from a puncture portion of the living body surface punctured with the needle point, a detecting section for detecting a predetermined component in the body fluid introduced through the introducing section, and a mounted section configured to be mounted to a component measuring device for measuring a quantity and/or property of the predetermined component detected by the detecting section;
a container comprising a mechanism containing section containing the puncture mechanism so that the needle point of the puncture mechanism is movable by the drive means, and a sampling implement containing section containing the body fluid sampling implement in a manner allowing the body fluid sampling implement to be removed from the sampling implement containing section; and
wherein the body fluid sampling implement is configured to be mounted to the component measuring device while the body fluid sampling implement is contained in the sampling implement containing section, and is thereafter removed from the sampling implement containing section while mounted to the component measuring device by spacing the container away from the component measuring device.

4. The body fluid sampling unit as set forth in claim 3, wherein the sampling implement containing section extends from the mechanism containing section, and the sampling implement containing section and the mechanism containing section are disposed coaxially.

5. The body fluid sampling unit as set forth in claim 4, wherein the sampling implement containing section is located on a side opposite to the direction of the needle point of the needle relative to the mechanism containing section.

6. The body fluid sampling unit as set forth in claim 3, wherein the drive means moves the needle in a puncturing direction to puncture the living body surface with the needle point, the body fluid sampling implement being removable from the sampling implement containing section in a direction opposite the puncturing direction of the needle.

7. The body fluid sampling unit as set forth in claim 3,
wherein the body fluid sampling implement is tentatively fixed to the sampling implement containing section, and
a force with which the sampling implement containing section fixes the body fluid sampling implement is smaller than a force of connection between the body fluid sampling implement and the component measuring device.

8. The body fluid sampling unit as set forth in claim 3, further comprising a cap covering the needle point of the needle and maintaining a sterile state of the needle point.

9. The body fluid sampling unit as set forth in claim 3,
wherein the mounted section possesses a bottomed tube shape;
the introducing section protrudes in a tubular form from a bottom part of the mounted section; and
the detecting section is disposed at the bottom part.

10. The body fluid sampling unit as set forth in claim 3, wherein the detecting section comprises a test paper carrying a reagent adapted to perform a color reaction with the predetermined component in the body fluid.

11. The body fluid sampling unit as set forth in claim 3, wherein the body fluid sampling unit is discarded after one time use in measuring the quantity and/or property of the predetermined component.

12. A body fluid sampling unit comprising:
a puncture mechanism comprising a needle possessing a sharp needle point at a distal end of the needle, and drive means for operating the needle to puncture a living body surface with the needle point;
a body fluid sampling implement comprising an introducing section for introducing a body fluid flowing out from a puncture portion of the living body surface punctured with the needle point, a detecting section for detecting a predetermined component in the body fluid introduced through the introducing section, and a mounted section configured to be mounted to a component measuring device for measuring a quantity and/or property of the predetermined component detected by the detecting section;

a container comprising a mechanism containing section containing the puncture mechanism so that the needle point of the puncture mechanism is movable by the drive means, and a sampling implement containing section containing the body fluid sampling implement in a manner allowing the body fluid sampling implement to be removed from the sampling implement containing section; and wherein the body fluid sampling implement is used by being removed from the sampling implement containing section and then being mounted to the component measuring device.

13. The body fluid sampling unit as set forth in claim 12, further comprising a cap covering the needle point of the needle and maintaining a sterile state of the needle point.

14. The body fluid sampling unit as set forth in claim 12, wherein the sampling implement containing section has an opening through which the body fluid sampling implement is movable into and out of the sampling implement containing section, the sampling implement containing section comprising a seal member sealing the opening in a gas-tight manner while the body fluid sampling implement is contained in the sampling implement containing section.

15. The body fluid sampling unit as set forth in claim 12, wherein the detecting section comprises a test paper carrying a reagent adapted to perform a color reaction with the predetermined component in the body fluid.

16. A body fluid sampling unit comprising:

a puncture mechanism comprising a needle possessing a sharp needle point at a distal end of the needle, and drive means for operating the needle to puncture a living body surface with the needle point;

a body fluid sampling implement comprising an introducing section for introducing a body fluid flowing out from a puncture portion of the living body surface punctured with the needle point, a detecting section for detecting a predetermined component in the body fluid introduced through the introducing section, and a mounted section configured to be mounted to a component measuring device for measuring a quantity and/or property of the predetermined component detected by the detecting section;

a container comprising a mechanism containing section containing the puncture mechanism so that the needle point of the puncture mechanism is movable by the drive means, and a sampling implement containing section containing the body fluid sampling implement in a manner allowing the body fluid sampling implement to be removed from the sampling implement containing section; and wherein the drive means includes a support section at which the needle is supported and a biasing section adapted to bias the support section, and wherein a biasing force to bias the support section is accumulated in the biasing section by pressing the body fluid sampling implement against the component measuring device when mounting the body fluid sampling implement to the component measuring device.

17. The body fluid sampling unit as set forth in claim 16, wherein the sampling implement containing section has an opening through which the body fluid sampling implement is movable into and out of the sampling implement containing section, the sampling implement containing section comprising a seal member sealing the opening in a gas-tight manner while the body fluid sampling implement is contained in the sampling implement containing section.

18. The body fluid sampling unit as set forth in claim 16, wherein the detecting section comprises a test paper carrying a reagent adapted to perform a color reaction with the predetermined component in the body fluid.

19. The body fluid sampling unit as set forth in claim 16, wherein the mounted section possesses a bottomed tube shape;

the introducing section protrudes in a tubular form from a bottom part of the mounted section; and the detecting section is disposed at the bottom part.

20. The body fluid sampling unit as set forth in claim 16, further comprising a cap covering the needle point of the needle and maintaining a sterile state of the needle point.

21. The body fluid sampling unit as set forth in claim 16, wherein the mechanism containing section includes an outer tube;

the sampling implement containing section includes an inner tube slidably positioned inside the outer tube for slidably moving in a longitudinal direction of the outer tube, the inner tube being connected to the puncture mechanism;

the body fluid sampling implement is mounted to the component measuring device by pushing the component measuring device towards the body fluid sampling implement; and during pushing of the component measuring device towards the body fluid sampling implement, the inner tube is pushed together with the body fluid sampling implement to slidably move inside the outer tube, whereby a biasing force of the biasing section is accumulated.

22. The body fluid sampling unit as set forth in claim 16, wherein the body fluid sampling implement is tentatively fixed to the sampling implement containing section, and a force with which the sampling implement containing section fixes the body fluid sampling implement is smaller than a force of connection between the body fluid sampling implement and the component measuring device.

23. A body fluid sampling unit comprising:

a puncture mechanism comprising a needle possessing a sharp needle point at a distal end of the needle, and drive means for operating the needle to puncture a living body surface with the needle point;

a body fluid sampling implement comprising an introducing section for introducing a body fluid flowing out from a puncture portion of the living body surface punctured with the needle point, a detecting section for detecting a predetermined component in the body fluid introduced through the introducing section, and a mounted section configured to be mounted to a component measuring device for measuring a quantity and/or property of the predetermined component detected by the detecting section;

a container comprising a mechanism containing section containing the puncture mechanism so that the needle point of the puncture mechanism is movable by the drive means, and a sampling implement containing section containing the body fluid sampling implement in a manner allowing the body fluid sampling implement to be removed from the sampling implement containing section; and wherein the sampling implement containing section has an opening through which the body fluid sampling implement is movable into and out of the sampling implement containing section, the sampling implement containing section comprising a seal member sealing the opening in a gas-tight manner while the body fluid sampling implement is contained in the sampling implement containing section.

24. The body fluid sampling unit as set forth in claim 23, further comprising a cap covering the needle point of the needle and maintaining a sterile state of the needle point.

25. The body fluid sampling unit as set forth in claim 23, wherein the detecting section comprises a test paper carrying a reagent adapted to perform a color reaction with the predetermined component in the body fluid.

* * * * *